US012533133B2

(12) United States Patent
Baxter, III et al.

(10) Patent No.: US 12,533,133 B2
(45) Date of Patent: Jan. 27, 2026

(54) STAPLING DEVICE WITH KNIFE MOVABLE TO A SHIELDED CONFIGURATION

(71) Applicant: Cilag GmbH International, Zug (CH)

(72) Inventors: Chester O. Baxter, III, Loveland, OH (US); Jerome R. Morgan, Cincinnati, OH (US); Frederick E. Shelton, IV, Hillsboro, OH (US); Charles J. Scheib, Loveland, OH (US); Michael J. Vendely, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/775,427

(22) Filed: Jul. 17, 2024

(65) Prior Publication Data

US 2024/0366225 A1 Nov. 7, 2024

Related U.S. Application Data

(63) Continuation of application No. 17/591,759, filed on Feb. 3, 2022, now Pat. No. 12,076,017, which is a continuation of application No. 16/544,045, filed on Aug. 19, 2019, now Pat. No. 11,284,898, which is a continuation of application No. 16/131,148, filed on (Continued)

(51) Int. Cl.

| | |
|---|---|
| ***A61B 17/10*** | (2006.01) |
| ***A61B 17/068*** | (2006.01) |
| ***A61B 17/072*** | (2006.01) |
| ***A61B 17/3209*** | (2006.01) |

(52) U.S. Cl.

CPC .......... *A61B 17/105* (2013.01); *A61B 17/068* (2013.01); *A61B 17/07207* (2013.01); *A61B 17/3209* (2013.01); *A61B 2017/07271* (2013.01); *A61B 2017/07278* (2013.01); *A61B 2017/07285* (2013.01); *A61B 17/07292* (2013.01)

(58) Field of Classification Search

None

See application file for complete search history.

(56) References Cited

U.S. PATENT DOCUMENTS 4,608,981 A 9/1986 Rothfuss et al.
4,805,823 A 2/1989 Rothfuss
(Continued)

FOREIGN PATENT DOCUMENTS

CN 202568350 U 12/2012
CN 103690212 A 4/2014

*Primary Examiner* — Tanzim Imam

(74) *Attorney, Agent, or Firm* — Lempia Summerfield Katz LLC

(57) ABSTRACT

An apparatus comprises a body, a shaft assembly, an end effector, a cartridge, and a staple driver actuator. The end effector is operable to manipulate tissue. The end effector comprises a lower jaw, a pivotable anvil, and a translating cutter. The translating cutter is operable to translate relative to the lower jaw and the anvil when the anvil is pivoted toward the lower jaw to manipulate tissue. The cartridge is insertable into the lower jaw and includes a plurality of staples. The staple driver actuator is disposed within the cartridge. The staple driver actuator comprises a secondary cutting element. The translating cutter of the end effector is operable to drive the staple driver actuator distally to staple and cut tissue substantially simultaneously.

18 Claims, 27 Drawing Sheets

Related U.S. Application Data

Sep. 14, 2018, now Pat. No. 11,123,069, which is a continuation of application No. 14/489,746, filed on Sep. 18, 2014, now Pat. No. 10,105,142.

(56) References Cited

U.S. PATENT DOCUMENTS

| | | | |
|---|---|---|---|
| 5,415,334 | A | 5/1995 | Williamson et al. |
| 5,465,895 | A | 11/1995 | Knodel et al. |
| 5,597,107 | A | 1/1997 | Knodel et al. |
| 5,632,432 | A | 5/1997 | Schulze et al. |
| 5,673,840 | A | 10/1997 | Schulze et al. |
| 5,704,534 | A | 1/1998 | Huitema et al. |
| 5,792,135 | A | 8/1998 | Madhani et al. |
| 5,814,055 | A | 9/1998 | Knodel et al. |
| 5,817,084 | A | 10/1998 | Jensen |
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,620,161 | B2 | 9/2003 | Schulze et al. |
| 6,783,524 | B2 | 8/2004 | Anderson et al. |
| 6,978,921 | B2 | 12/2005 | Shelton, IV et al. |
| 7,000,818 | B2 | 2/2006 | Shelton, IV et al. |
| 7,143,923 | B2 | 12/2006 | Shelton, IV et al. |
| 7,278,563 | B1 | 10/2007 | Green |
| 7,303,108 | B2 | 12/2007 | Shelton, IV |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,524,320 | B2 | 4/2009 | Tierney et al. |
| 7,644,848 | B2 | 1/2010 | Swayze et al. |
| 7,691,098 | B2 | 4/2010 | Wallace et al. |
| 7,721,930 | B2 | 5/2010 | McKenna et al. |
| 7,806,891 | B2 | 10/2010 | Nowlin et al. |
| 8,011,555 | B2 | 9/2011 | Tarinelli et al. |
| 8,167,898 | B1 | 5/2012 | Schaller et al. |
| 8,210,411 | B2 | 7/2012 | Yates et al. |
| 8,365,975 | B1 | 2/2013 | Manoux et al. |
| 8,408,439 | B2 | 4/2013 | Huang et al. |
| 8,414,577 | B2 * | 4/2013 | Boudreaux ............ A61B 46/10 606/41 |
| 8,453,914 | B2 | 6/2013 | Laurent et al. |
| 8,479,969 | B2 | 7/2013 | Shelton, IV |
| 8,573,461 | B2 | 11/2013 | Shelton, IV et al. |
| 8,573,465 | B2 | 11/2013 | Shelton, IV |
| 8,602,288 | B2 | 12/2013 | Shelton, IV et al. |
| 8,616,431 | B2 | 12/2013 | Timm et al. |
| 8,657,177 | B2 | 2/2014 | Scirica et al. |
| 8,695,866 | B2 | 4/2014 | Leimbach et al. |
| 8,783,541 | B2 | 7/2014 | Shelton, IV et al. |
| 8,800,838 | B2 | 8/2014 | Shelton, IV |
| 8,814,025 | B2 | 8/2014 | Miller et al. |
| 8,820,605 | B2 | 9/2014 | Shelton, IV |
| 8,844,789 | B2 | 9/2014 | Shelton, IV et al. |
| 8,899,464 | B2 | 12/2014 | Hueil et al. |
| 8,945,163 | B2 | 2/2015 | Voegele et al. |
| 8,967,443 | B2 | 3/2015 | McCuen |
| 8,973,805 | B2 | 3/2015 | Scirica et al. |
| 8,991,678 | B2 | 3/2015 | Wellman et al. |
| 8,998,060 | B2 | 4/2015 | Bruewer et al. |
| 9,101,359 | B2 | 8/2015 | Smith et al. |
| 9,186,142 | B2 | 11/2015 | Fanelli et al. |
| 9,198,644 | B2 | 12/2015 | Balek et al. |
| 9,289,210 | B2 | 3/2016 | Baxter, III et al. |
| 9,301,759 | B2 | 4/2016 | Spivey et al. |
| 9,386,983 | B2 | 7/2016 | Swensgard et al. |
| 9,386,984 | B2 | 7/2016 | Aronhalt et al. |
| 9,386,985 | B2 | 7/2016 | Koch, Jr. et al. |
| 9,393,018 | B2 | 7/2016 | Wang et al. |
| 9,492,170 | B2 | 11/2016 | Bear et al. |
| 9,517,065 | B2 | 12/2016 | Simms et al. |
| 9,549,733 | B2 | 1/2017 | Knodel |
| 9,622,746 | B2 | 4/2017 | Simms et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,861,361 | B2 | 1/2018 | Aronhalt et al. |
| 9,867,615 | B2 | 1/2018 | Fanelli et al. |
| 9,924,941 | B2 | 3/2018 | Burbank |
| 9,974,541 | B2 | 5/2018 | Calderoni |
| 9,999,408 | B2 | 6/2018 | Boudreaux et al. |
| 10,092,292 | B2 | 10/2018 | Boudreaux et al. |
| 10,105,142 | B2 | 10/2018 | Baxter, III et al. |
| 10,194,908 | B2 | 2/2019 | Duque et al. |
| 10,258,336 | B2 | 4/2019 | Baxter, III et al. |
| 10,292,701 | B2 | 5/2019 | Scheib et al. |
| 10,335,147 | B2 | 7/2019 | Rector et al. |
| 11,123,069 | B2 | 9/2021 | Baxter, III et al. |
| 11,284,898 | B2 | 3/2022 | Baxter, III et al. |
| 12,076,017 | B2 | 9/2024 | Baxter, III et al. |
| 2004/0199181 | A1 | 10/2004 | Knodel et al. |
| 2007/0194079 | A1 | 8/2007 | Hueil et al. |
| 2008/0167671 | A1 * | 7/2008 | Giordano ......... A61B 17/07207 606/167 |
| 2009/0112234 | A1 | 4/2009 | Crainich et al. |
| 2009/0118762 | A1 | 5/2009 | Crainch et al. |
| 2009/0206137 | A1 | 8/2009 | Hall et al. |
| 2010/0243707 | A1 | 9/2010 | Olson et al. |
| 2012/0248169 | A1 * | 10/2012 | Widenhouse .... A61B 17/07207 227/175.1 |
| 2012/0292367 | A1 | 11/2012 | Morgan et al. |
| 2013/0068816 | A1 | 3/2013 | Mandakolathur Vasudevan et al. |
| 2013/0075447 | A1 | 3/2013 | Weisenburgh, II et al. |
| 2013/0098969 | A1 * | 4/2013 | Scirica ............ A61B 17/07207 227/180.1 |
| 2013/0313305 | A1 * | 11/2013 | Scirica ............ A61B 17/07207 227/180.1 |
| 2014/0183244 | A1 | 7/2014 | Duque et al. |
| 2015/0230794 | A1 | 8/2015 | Wellman et al. |
| 2016/0074035 | A1 | 3/2016 | Whitman et al. |
| 2017/0079651 | A1 * | 3/2017 | Duque ................ A61B 17/068 |
| 2018/0085120 | A1 * | 3/2018 | Viola .............. A61B 17/00491 |
| 2018/0168572 | A1 * | 6/2018 | Burbank ............... A61B 50/13 |
| 2018/0317905 | A1 | 11/2018 | Olson et al. |

* cited by examiner

STAPLING DEVICE WITH KNIFE MOVABLE TO A SHIELDED CONFIGURATION

CROSS-REFERENCE TO RELATED APPLICATIONS

This application is a continuation application claiming priority under 35 U.S.C. § 120 to U.S. patent application Ser. No. 17/591,759, entitled SURGICAL STAPLER WITH PLURALITY OF CUTTING ELEMENTS, filed Feb. 3, 2022, now U.S. Patent Application Publication No. 2022/0233194, which is a continuation application claiming priority under 35 U.S.C. § 120 to U.S. patent application Ser. No. 16/544,045, entitled SURGICAL STAPLER WITH PLURALITY OF CUTTING ELEMENTS, filed Aug. 19, 2019, which issued on Mar. 29, 2022 as U.S. Pat. No. 11,284,898, which is a continuation application claiming priority under 35 U.S.C. § 120 to U.S. patent application Ser. No. 16/131,148, entitled SURGICAL STAPLER WITH PLURALITY OF CUTTING ELEMENTS, filed Sep. 14, 2018, which issued on Sep. 21, 2021 as U.S. Pat. No. 11,123,069, which is a continuation application claiming priority under 35 U.S.C. § 120 to U.S. patent application Ser. No. 14/489,746, entitled SURGICAL STAPLER WITH PLURALITY OF CUTTING ELEMENTS, filed Sep. 18, 2014, which issued on Oct. 23, 2018 as U.S. Pat. No. 10,105,142, the entire disclosures of which are hereby incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled POCKET CONFIGURATION FOR INTERNAL ORGAN STAPLERS, issued Feb. 21, 1989; U.S. Pat. No. 5,415,334, entitled SURGICAL STAPLER AND STAPLE CARTRIDGE, issued May 16, 1995; U.S. Pat. No. 5,465,895, entitled SURGICAL STAPLER INSTRUMENT, issued Nov. 14, 1995; U.S. Pat. No. 5,597,107, entitled SURGICAL STAPLER INSTRUMENT, issued Jan. 28, 1997; U.S. Pat. No. 5,632,432, entitled SURGICAL INSTRUMENT, issued May 27, 1997; U.S. Pat. No. 5,673,840, entitled SURGICAL INSTRUMENT, issued Oct. 7, 1997; U.S. Pat. No. 5,704,534, entitled ARTICULATION ASSEMBLY FOR SURGICAL INSTRUMENTS, issued Jan. 6, 1998; U.S. Pat. No. 5,814,055, entitled SURGICAL CLAMPING MECHANISM, issued Sep. 29, 1998; U.S. Pat. No. 6,978,921, entitled SURGICAL STAPLING INSTRUMENT INCORPORATING AN E-BEAM FIRING MECHANISM, issued Dec. 27, 2005; U.S. Pat. No. 7,000,818, entitled SURGICAL STAPLING INSTRUMENT HAVING SEPARATE DISTINCT CLOSING AND FIRING SYSTEMS, issued Feb. 21, 2006; U.S. Pat. No. 7,143,923, entitled SURGICAL STAPLING INSTRUMENT HAVING A FIRING LOCKOUT FOR AN UNCLOSED ANVIL, issued Dec. 5, 2006; U.S. Pat. No. 7,303,108, entitled SURGICAL STAPLING INSTRUMENT INCORPORATING A MULTI-STROKE FIRING MECHANISM WITH A FLEXIBLE RACK, issued Dec. 4, 2007; U.S. Pat. No. 7,367,485, entitled SURGICAL STAPLING INSTRUMENT INCORPORATING A MULTISTROKE FIRING MECHANISM HAVING A ROTARY TRANSMISSION, issued May 6, 2008; U.S. Pat. No. 7,380,695, entitled SURGICAL STAPLING INSTRUMENT HAVING A SINGLE LOCKOUT MECHANISM FOR PREVENTION OF FIRING, issued Jun. 3, 2008; U.S. Pat. No. 7,380,696, entitled ARTICULATING SURGICAL STAPLING INSTRUMENT INCORPORATING A TWO-PIECE E-BEAM FIRING MECHANISM, issued Jun. 3, 2008; U.S. Pat. No. 7,404,508, entitled SURGICAL STAPLING AND CUTTING DEVICE, issued Jul. 29, 2008; U.S. Pat. No. 7,434,715, entitled SURGICAL STAPLING INSTRUMENT HAVING MULTISTROKE FIRING WITH OPENING LOCKOUT, issued Oct. 14, 2008; U.S. Pat. No. 7,721,930, entitled DISPOSABLE CARTRIDGE WITH ADHESIVE FOR USE WITH A STAPLING DEVICE, issued May 25, 2010; U.S. Pat. No. 8,408,439, entitled SURGICAL STAPLING INSTRUMENT WITH AN ARTICULATABLE END EFFECTOR, issued Apr. 2, 2013; and U.S. Pat. No. 8,453,914, entitled MOTOR-DRIVEN SURGICAL CUTTING INSTRUMENT WITH ELECTRIC ACTUATOR DIRECTIONAL CONTROL ASSEMBLY, issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled SURGICAL INSTRUMENT END EFFECTOR ARTICULATION DRIVE WITH PINION AND OPPOSING RACKS, published Aug. 28, 2014, now U.S. Pat. No. 9,186,142; U.S. Patent Application Publication No. 2014/0239041, entitled LOCKOUT FEATURE FOR MOVABLE CUTTING MEMBER OF SURGICAL INSTRUMENT, published Aug. 28, 2014, now U.S. Pat. No. 9,717,497; U.S.

Patent Application Publication No. 2014/0239042, entitled INTEGRATED TISSUE POSITIONING AND JAW ALIGNMENT FEATURES FOR SURGICAL STAPLER, published Aug. 28, 2014, now U.S. Pat. No. 9,517,065; U.S. Patent Application Publication No. 2014/0239036, entitled JAW CLOSURE FEATURE FOR END EFFECTOR OF SURGICAL INSTRUMENT, published Aug. 28, 2014, now U.S. Pat. No. 9,839,421; U.S. Patent Application Publication No. 2014/0239040, entitled SURGICAL INSTRUMENT WITH ARTICULATION LOCK HAVING A DETENTING BINARY SPRING, published Aug. 28, 2014, now U.S. Pat. No. 9,867,615; U.S. Patent Application Publication No. 2014/0239043, entitled DISTAL TIP FEATURES FOR END EFFECTOR OF SURGICAL INSTRUMENT, published Aug. 28, 2014, now U.S. Pat. No. 9,622,746; U.S. Patent Application Publication No. 2014/0239037, entitled STAPLE FORMING FEATURES FOR SURGICAL STAPLING INSTRUMENT, published Aug. 28, 2014, now U.S. Pat. No. 10,092,292; U.S. Patent Application Publication No. 2014/0239038, entitled SURGICAL INSTRUMENT WITH MULTI-DIAMETER SHAFT, published Aug. 28, 2014, now U.S. Pat. No. 9,795,379; and U.S. Patent Application Publication No. 2014/0239044, entitled INSTALLATION FEATURES FOR SURGICAL INSTRUMENT END EFFECTOR CARTRIDGE, published Aug. 28, 2014, now U.S. Pat. No. 9,808,248. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
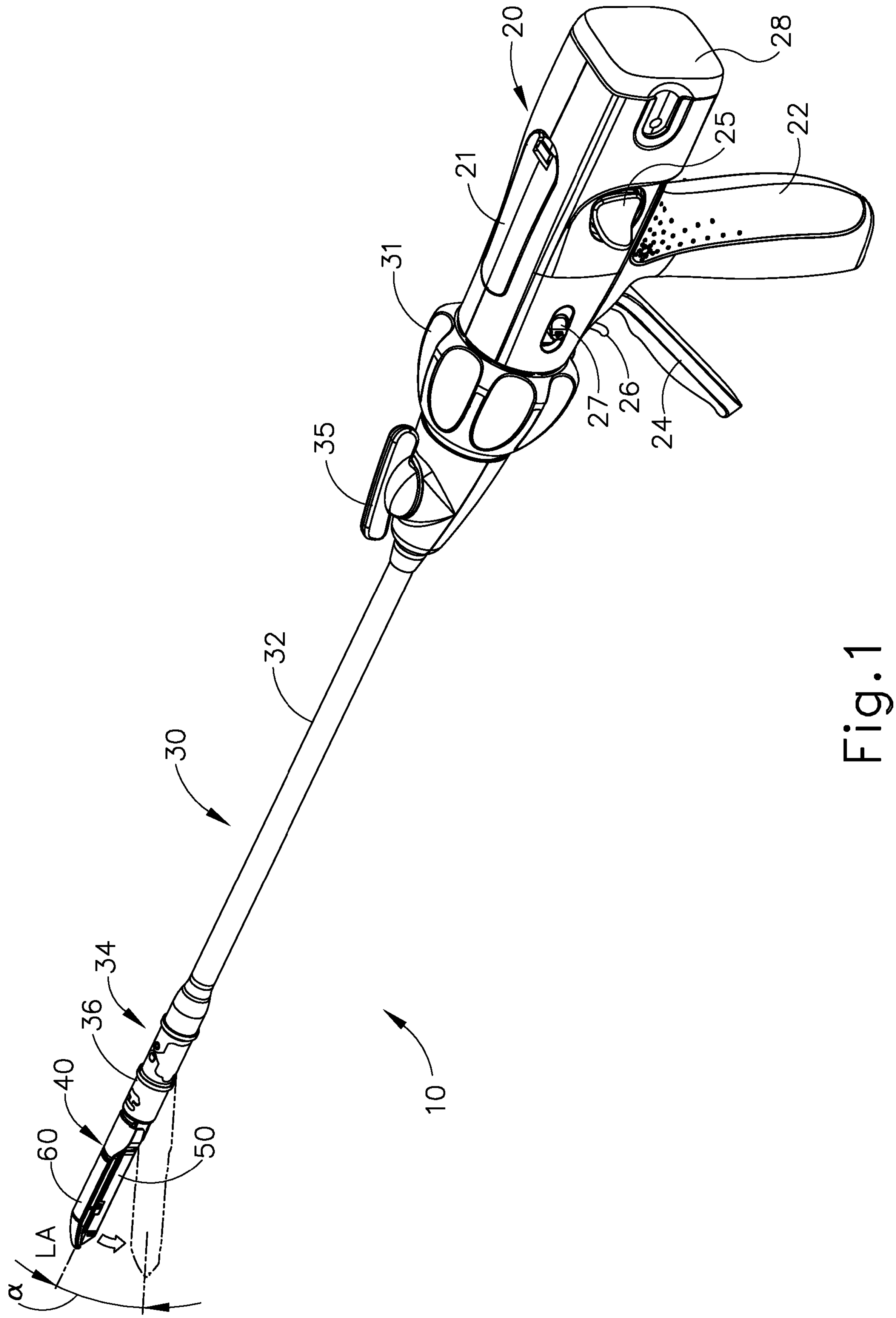
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
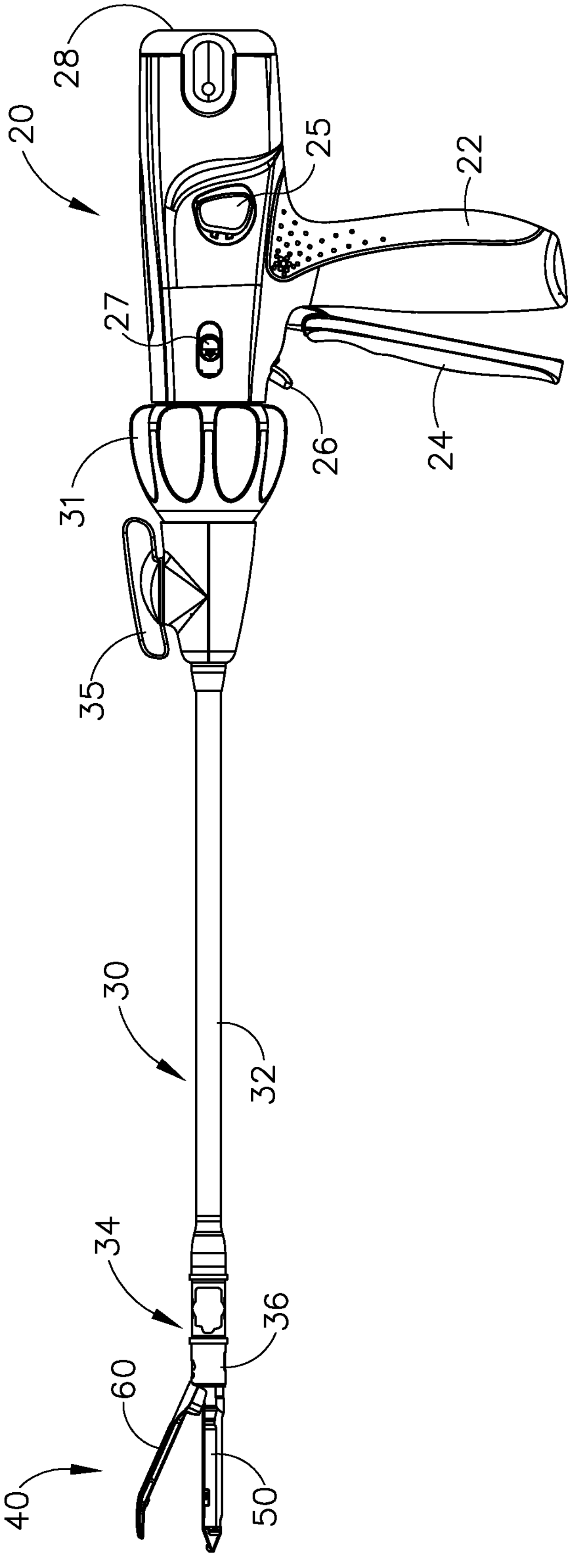
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
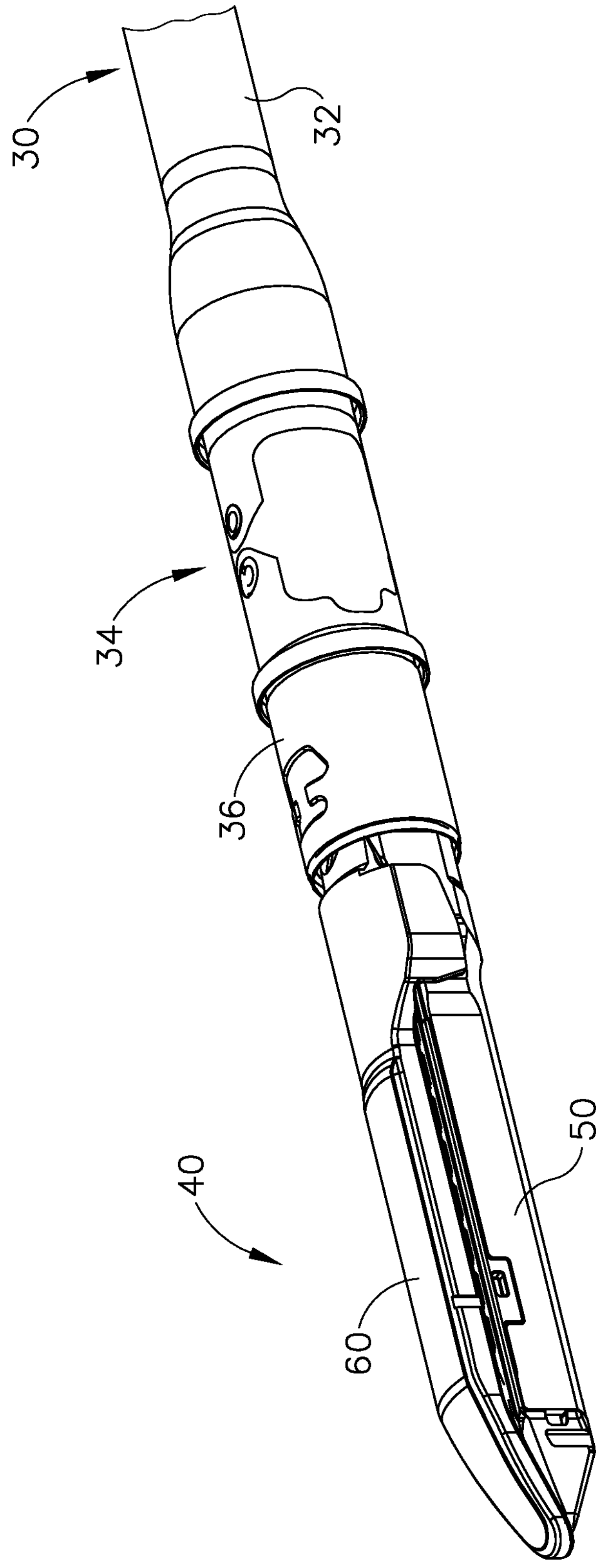
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle ($\alpha$). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. patent application Ser. No. 13/780,067, entitled SURGICAL INSTRUMENT END EFFECTOR ARTICULATION DRIVE WITH PINION AND OPPOSING RACKS, filed Feb. 28, 2013, now U.S. Pat. No. 9,186,142, the disclosure of which is incorporated by reference herein. Articulation section (34) may also be constructed and operable in accordance with at least some of the teachings of U.S. patent application Ser. No. 14/314,125, entitled ARTICULATION DRIVE FEATURES FOR SURGICAL STAPLER, filed Jun. 25, 2014, now U.S. Pat. No. 10,292,701, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. patent application Ser. No. 13/780,402, entitled SURGICAL INSTRUMENT WITH MULTI-DIAMETER SHAFT, filed Feb. 28, 2013, now U.S. Pat. No. 9,795,379, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. patent application Ser. No. 13/780,417, entitled INSTALLATION FEATURES FOR SURGICAL INSTRUMENT END EFFECTOR CARTRIDGE, filed Feb. 28, 2013, now U.S. Pat. No. 9,808,248, the disclosure of which is incorporated by reference herein. Other suitable forms that lower jaw (50) may take will be apparent to those of ordinary skill in the art in view of the teachings herein.

Figure 4:
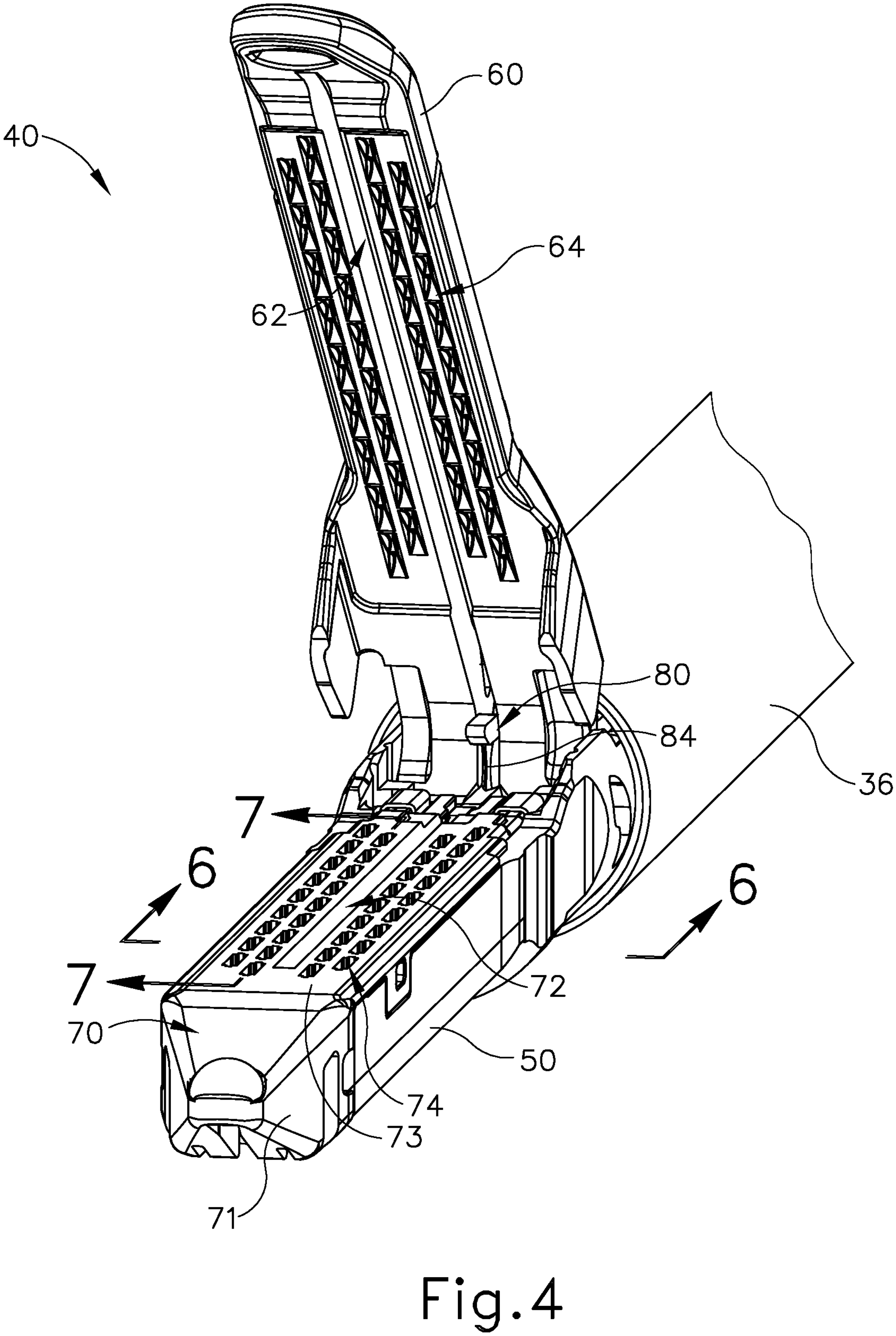
FIG. 4 depicts a perspective view of the end effector of FIG. 3, with the end effector in an open configuration.
Figure 5:
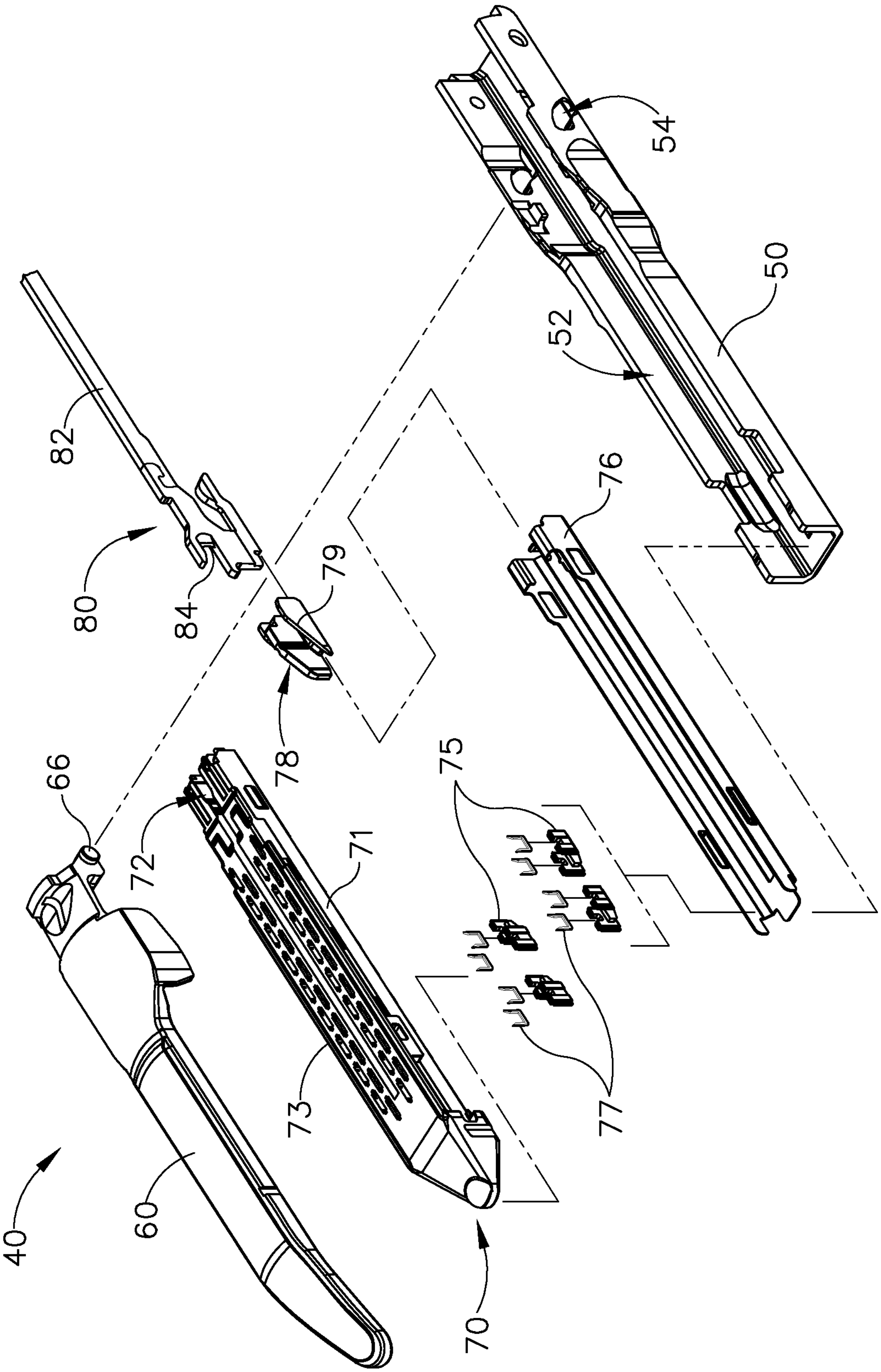
FIG. 5 depicts an exploded perspective view of the end effector of FIG. 3.
Figure 6:
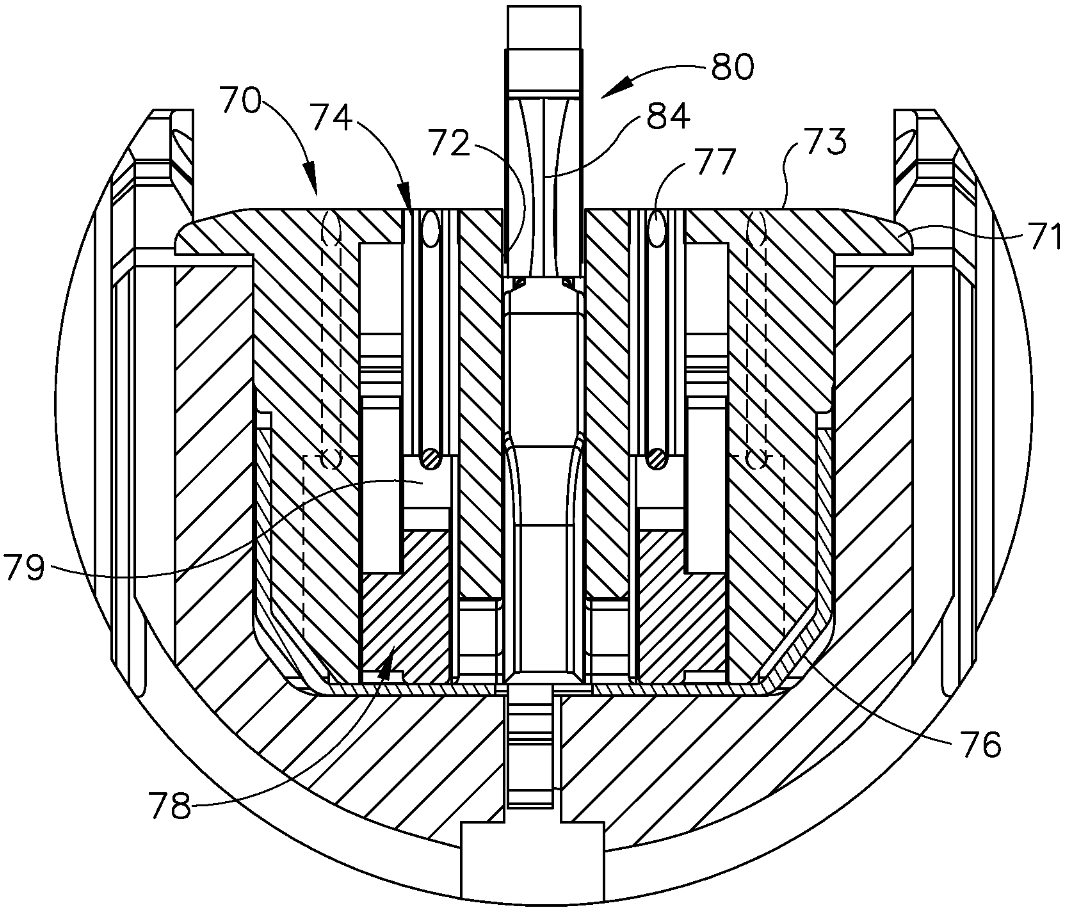
FIG. 6 depicts a cross-sectional end view of the end effector of FIG. 3, taken along line 6-6 of FIG. 4.
Figure 7A:
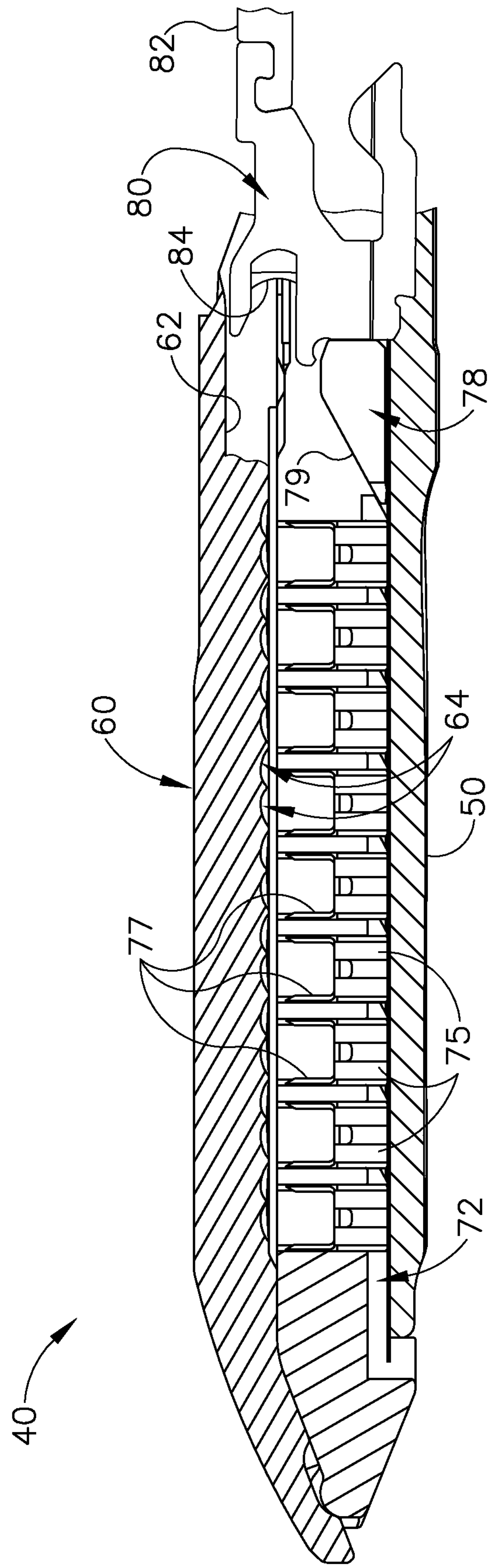
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U.S. patent application Ser. No. 13/780,106, entitled INTEGRATED TISSUE POSITIONING AND JAW ALIGNMENT FEATURES FOR SURGICAL STAPLER, filed Feb. 28, 2013, now U.S. Pat. No. 9,517,065, the disclosure of which is incorporated by reference herein. In addition or in the alternative, staple cartridge (70) may be constructed and operable in accordance with at least some of the teachings of U.S. patent application Ser. No. 13/780,417, entitled INSTALLATION FEATURES FOR SURGICAL INSTRUMENT END EFFECTOR CARTRIDGE, filed Feb. 28, 2013, now U.S. Pat. No. 9,808,248, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. patent application Ser. No. 13/780,106, entitled INTEGRATED TISSUE POSITIONING AND JAW ALIGNMENT FEATURES FOR SURGICAL STAPLER, filed Feb. 28, 2013, now U.S. Pat. No. 9,517,065; at least some of the teachings of U.S. patent application Ser. No. 13/780,120, entitled JAW CLOSURE FEATURE FOR END EFFECTOR OF SURGICAL INSTRUMENT, filed Feb. 28, 2013, now U.S. Pat. No. 9,839,421; and/or at least some of the teachings of U.S. patent application Ser. No. 13/780,379, entitled STAPLE FORMING FEATURES FOR SURGICAL STAPLING INSTRUMENT, filed Feb. 28, 2013, now U.S. Pat. No. 10,092,292, the disclosure of which is incorporated by reference herein. Other suitable forms that anvil (60) may take will be apparent to those of ordinary skill in the art in view of the teachings herein.

Figure 7B:
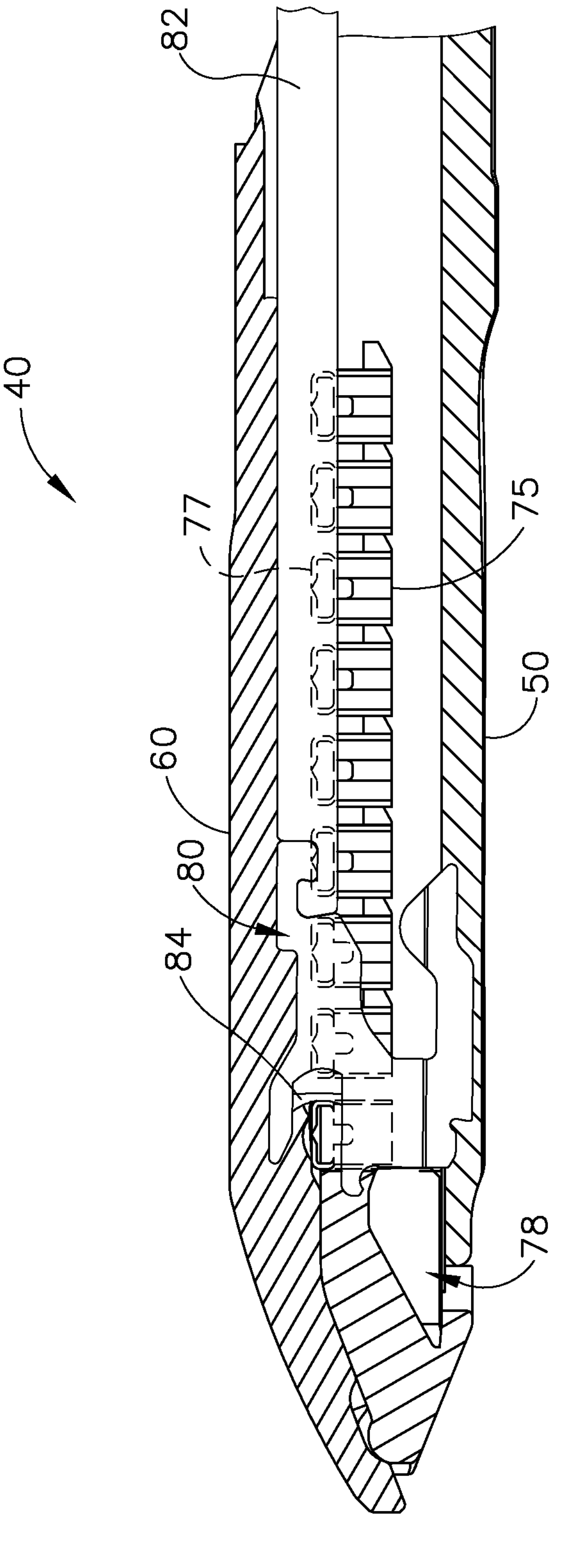
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. patent application Ser. No. 13/780,082, entitled LOCKOUT FEATURE FOR MOVABLE CUTTING MEMBER OF SURGICAL INSTRUMENT, filed Feb. 28, 2013, now U.S. Pat. No. 9,717,497, the disclosure of which is incorporated by reference herein; and/or at least some of the teachings of U.S. patent application Ser. No. 14/314,108, entitled METHOD OF USING LOCKOUT FEATURES FOR SURGICAL STAPLER CARTRIDGE, filed on Jun. 25, 2014, now U.S. Pat. No. 10,335,147, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. patent application Ser. No. 13/780,120, entitled JAW CLOSURE FEATURE FOR END EFFECTOR OF SURGICAL INSTRUMENT, filed Feb. 28, 2013, now U.S. Pat. No. 9,839,421, the disclosure of which is incorporated by reference herein; and/or in accordance with at least some of the teachings of U.S. patent application Ser. No. 14/314,108, entitled JAW OPENING FEATURE FOR SURGICAL STAPLER, filed on Jun. 25, 2014, now U.S. Pat. No. 10,335,147, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

Figure 9:
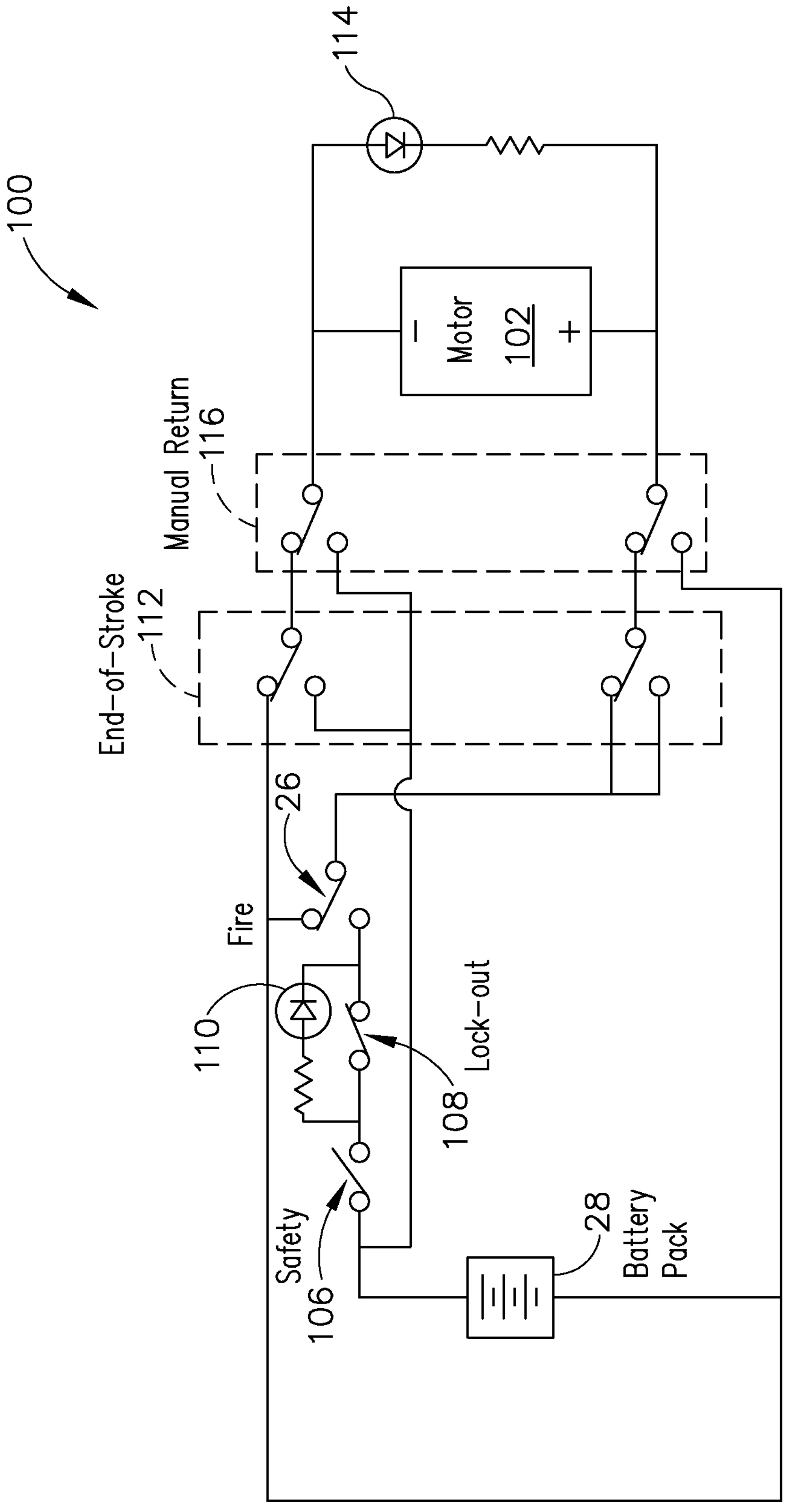
FIG. 9 depicts a schematic view of an exemplary control circuit for use in the instrument of FIG. 1.

In the present example, instrument (10) provides motorized control of firing beam (82). FIGS. 9-12 show exemplary components that may be used to provide motorized control of firing beam (82). In particular, FIG. 9 shows an exemplary control circuit (100) that may be used to power an electric motor (102) with electric power from a battery pack (28) (also shown in FIGS. 1-2). Electric motor (102) is operable to translate firing beam (82) longitudinally as will be described in greater detail below. It should be understood that the entire control circuit (100), including motor (102) and battery pack (28), may be housed within handle assembly (20). FIG. 9 shows firing trigger (26) as an open switch, though it should be understood that this switch is closed when firing trigger (26) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle assembly (20). Safety switch (106) may also provide a mechanical lockout of firing trigger (26), such that firing trigger (26) is mechanically blocked from actuation until safety switch (106) is actuated.

Circuit (100) of the present example also includes a lockout switch (108), which is configured to be closed by default but is automatically opened in response to a lockout condition. By way of example only, a lockout condition may include one or more of the following: the absence of a cartridge (70) in lower jaw (50), the presence of a spent (e.g., previously fired) cartridge (70) in lower jaw (50), an insufficiently closed anvil (60), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled ELECTRONIC LOCKOUTS AND SURGICAL INSTRUMENT INCLUDING SAME, issued Jan. 12, 2010, the disclosure of which is incorporated by reference herein.

Figure 12:
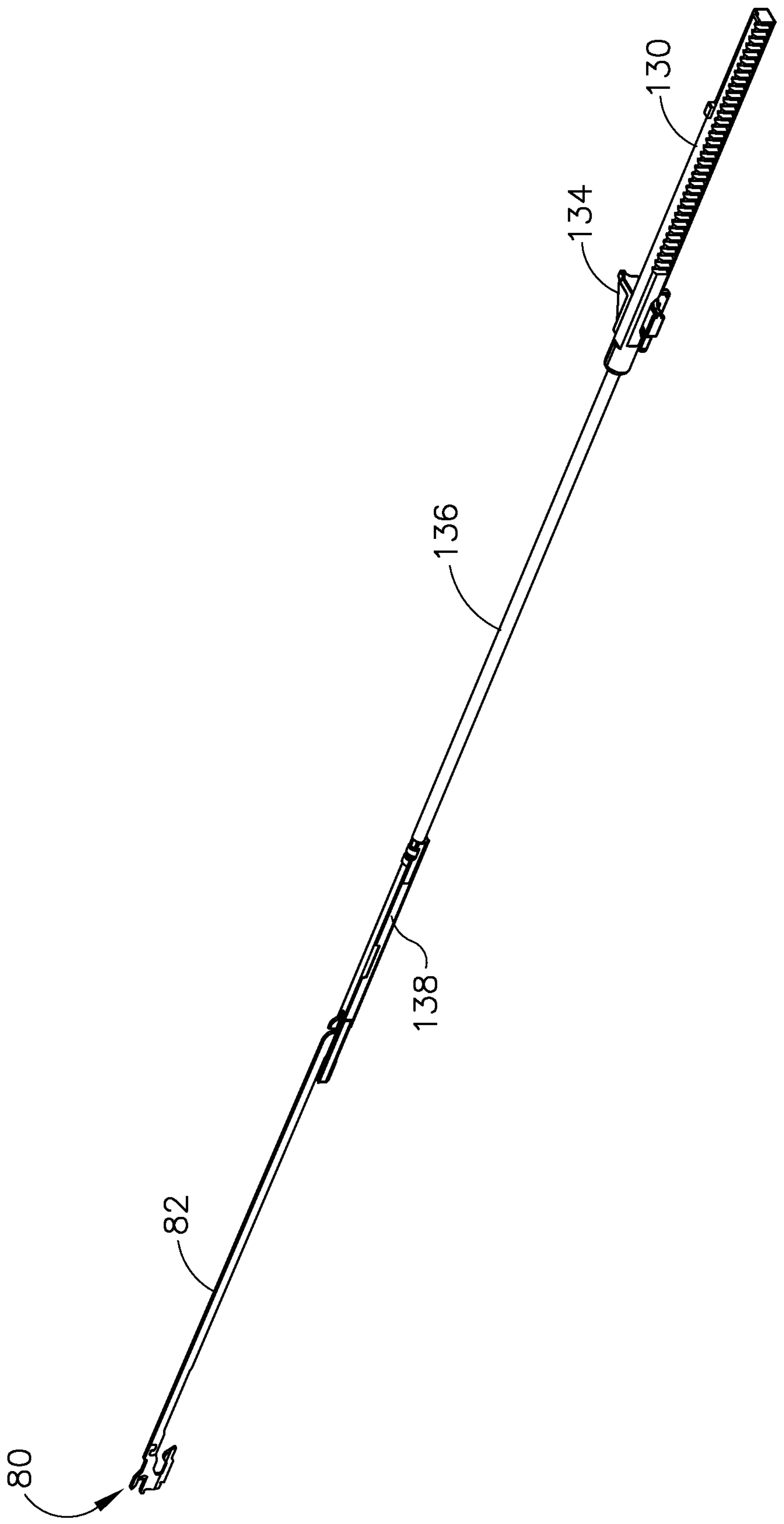
FIG. 12 depicts a perspective view of an elongate member from the drive assembly of FIG. 11, coupled with the firing beam.

Once firing beam (82) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (26) at this stage of operation. In this operational state, current flows through a reverse direction indicator (114) (e.g., an LED, etc.) to provide a visual indication to the operator that motor (102) rotation has been reversed. In the present example, and as best seen in FIG. 12, a switch actuation arm (134) extends laterally from rack member (130), and is positioned to engage end-of-stroke switch (112) when firing beam (82) reaches a distal-most position (e.g., after tissue (90) has been severed and staples (77) have been driven into tissue (90)). Various other suitable ways in which end-of-stroke switch (112) may be automatically switched to a closed position when firing beam (82) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle assembly (20) of the present example also includes a manual return switch (116), which is also shown in circuit (100). In the present example, return switch is activated by actuating reverse switch (27), which is shown on handle assembly (20) in FIG. 1. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114). In some versions, handle assembly (20) further includes a mechanical return feature that enables the operator to manually reverse firing beam (82) and thereby retract firing beam (82) mechanically. In the present example, this manual return feature comprises a lever that is covered by a removable panel (21) as shown in FIG. 1. Manual return switch (116) and the mechanical return feature are each configured to act as a "bailout" feature, enabling the operator to quickly begin retracting firing beam (82) proximally during a firing stroke. In other words, manual return switch (116) or the mechanical return feature may be actuated when firing beam (82) has only been partially advanced distally.

In some versions, one or more of switches (26, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled MOTOR-DRIVEN SURGICAL INSTRUMENT, issued Jul. 3, 2012, the disclosure of which is incorporated by reference herein.

Figure 10:
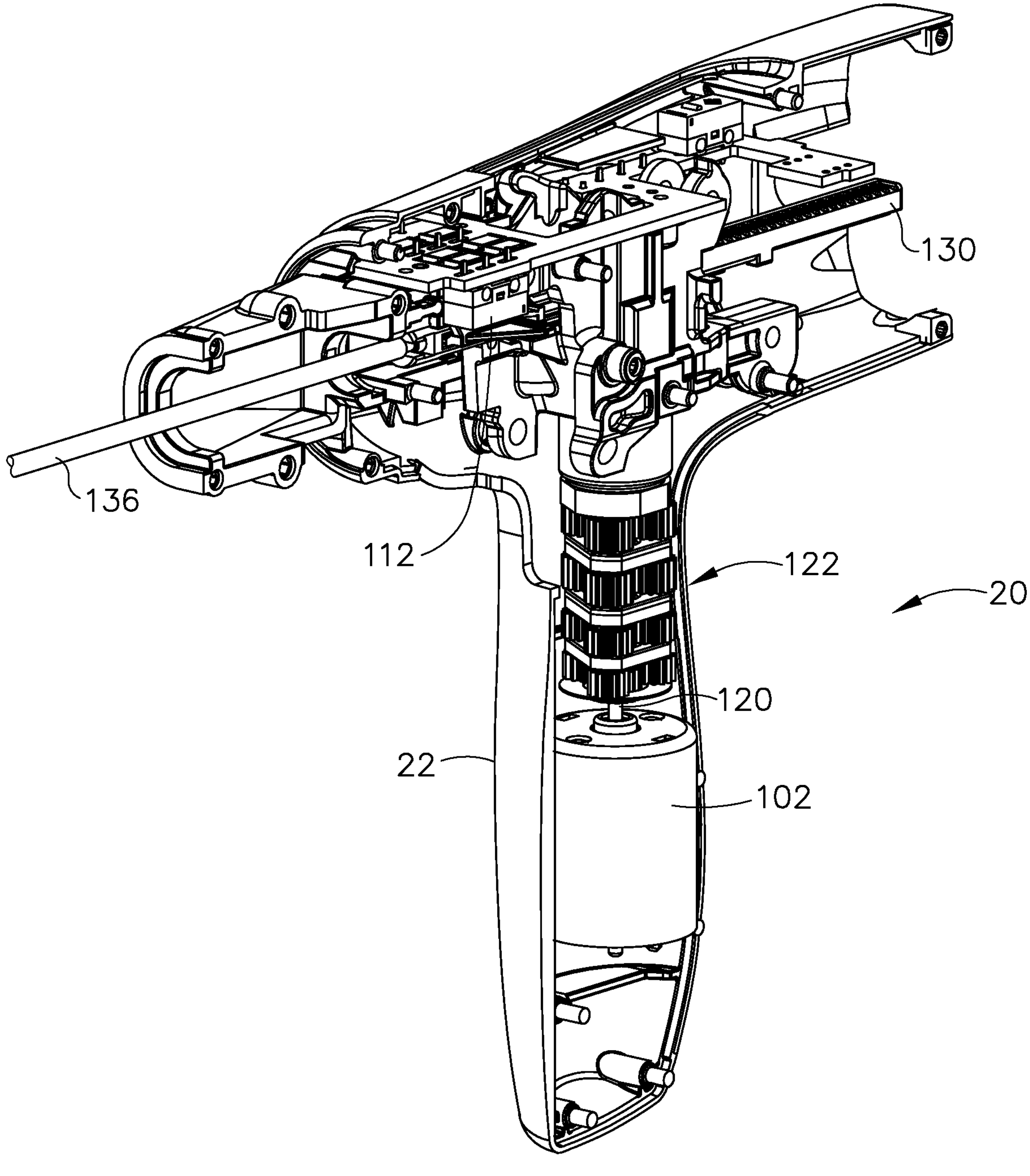
FIG. 10 depicts a perspective view of the handle assembly of the instrument of FIG. 1, with a housing half and some internal components removed.
Figure 11:
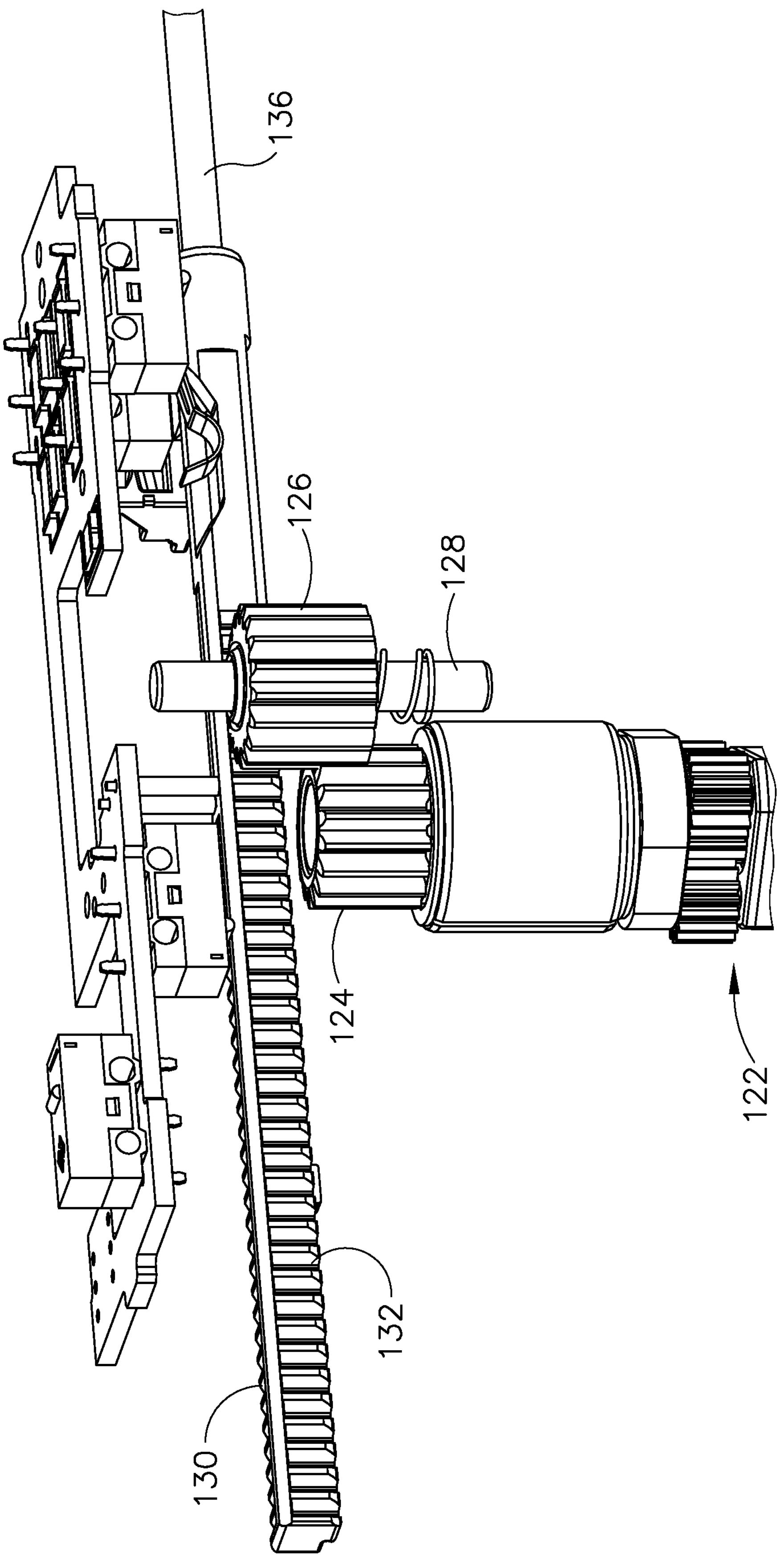
FIG. 11 depicts a perspective view of drive assembly components from the handle assembly of FIG. 10.

FIG. 10 shows motor (102) positioned within pistol grip (22) of handle assembly (20). Alternatively, motor (102) may be positioned elsewhere within handle assembly (20). Motor (102) has a drive shaft (120) that is coupled with a gear assembly (122). Thus, when motor (102) is activated, drive shaft (120) actuates gear assembly (122). As shown in FIG. 11, gear assembly (122) is in communication with a drive gear (124), which meshes with an idler pinion (126). Pinion (126) is disposed on a shaft (128) that is supported within handle assembly (20) and that is oriented parallel to drive shaft (120) of motor (102). Pinion (126) is further engaged with a rack member (130). In particular, pinion (126) meshes with teeth (132) at the proximal end of rack member (130). Rack member (130) is slidably supported in handle assembly (20). It should be understood from the foregoing that, when motor (102) is activated, the corresponding rotation of drive shaft (120) is communicated to pinion (126) via gear assembly (122), and the corresponding rotation of pinion (126) is converted to translation of rack member (130) by teeth (132). As shown in FIGS. 10-12, an elongate member (136) extends distally from rack member (130). As shown in FIG. 12, a coupling member (138) joins firing beam (82) with elongate member (136). Rack member (130), elongate member (136), coupling member (138), firing beam (82), and knife member (80) all translate together relative to handle assembly (20) in response to activation of motor (102). In other words, activation of motor (102) ultimately causes firing beam (82) to translate longitudinally, the direction of such translation depending on the direction of rotation of drive shaft (120).

It should be understood that a distal portion of elongate member (136), coupling member (138), and firing beam (82) extend through shaft assembly (30). A portion of firing beam (82) also extends through articulation section (34). In some versions, rack member (130), elongate member (136), and coupling member (138) are all substantially straight and rigid; while firing beam (82) has sufficient flexibility to bend at articulation section (34) and translate longitudinally through articulation section (34) when articulation section (34) is in a bent or articulated state.

In addition to or in lieu of the foregoing, the features operable to drive firing beam (82) may be configured in accordance with at least some of the teachings of U.S. Pat. No. 8,453,914, the disclosure of which is incorporated by reference herein. Other suitable components, features, and configurations for providing motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be actuated in accordance with at least some of the teachings of any other reference cited herein.

Figure 8:
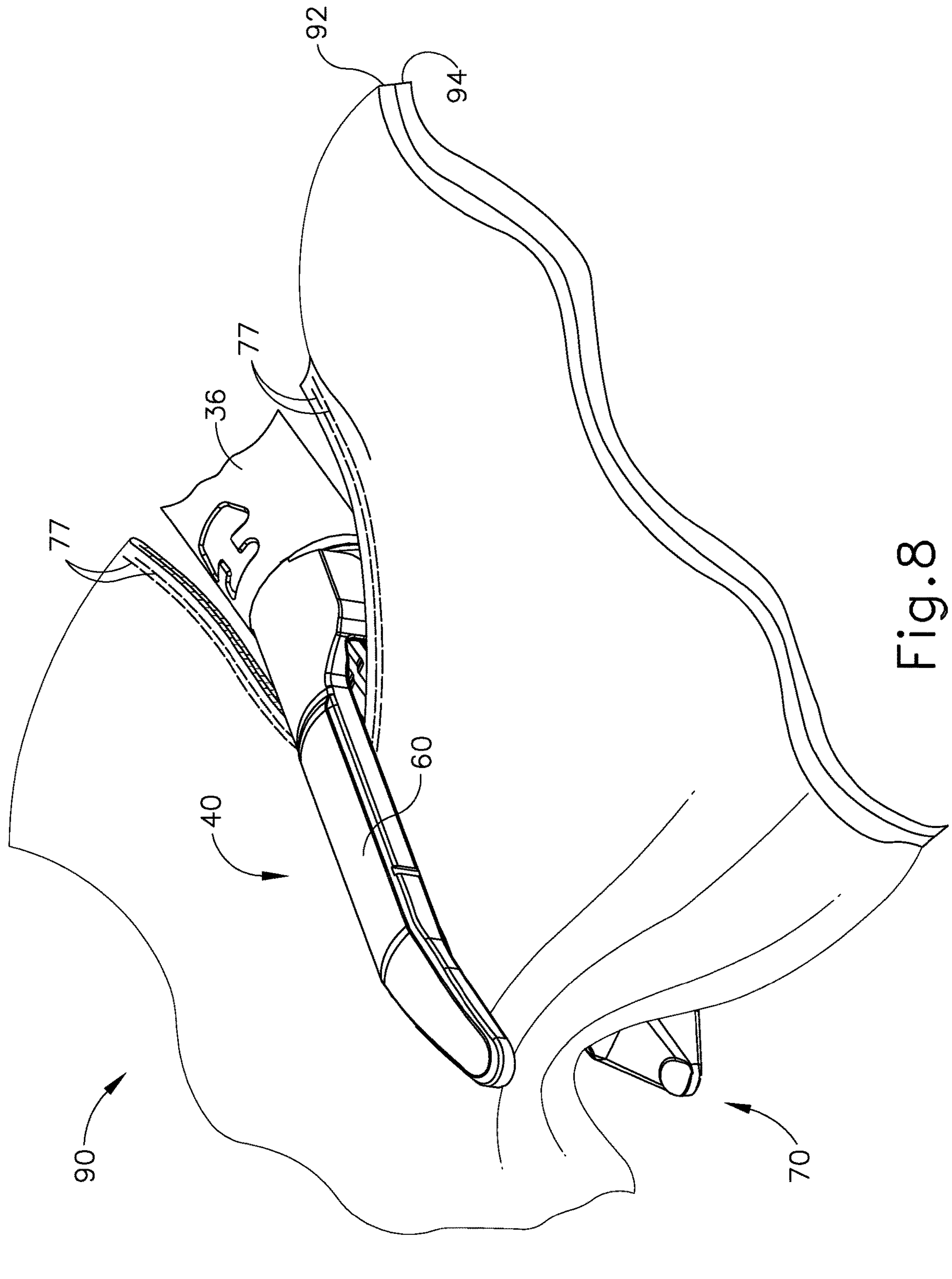
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may sever tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples (77). While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Staple Cartridge

Figure 13:
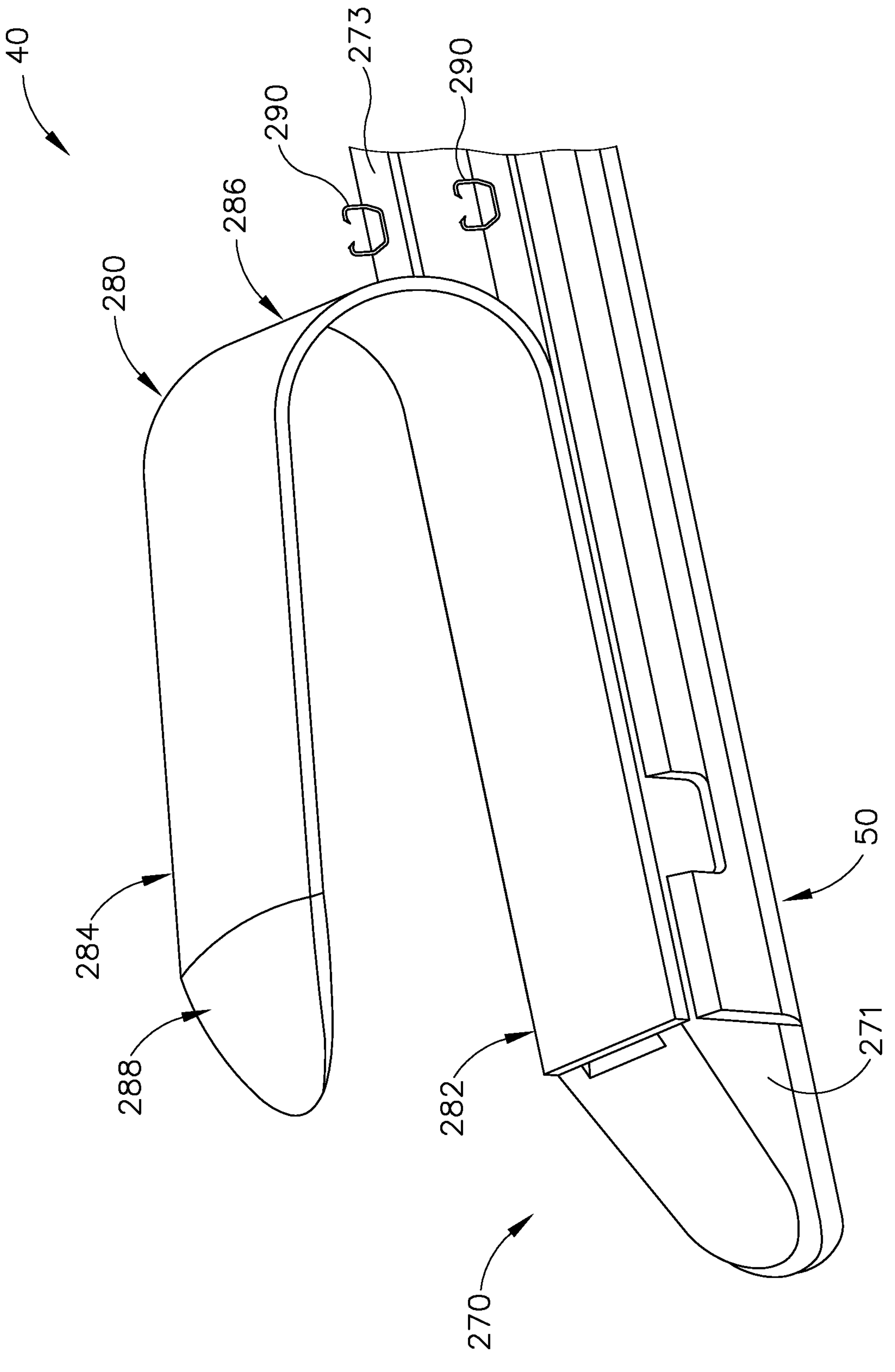
FIG. 13 depicts a partial perspective view of an exemplary staple cartridge of the end effector of FIG. 3, with an exemplary buttress disposed above and on an exterior top surface of the staple cartridge.
Figure 14:
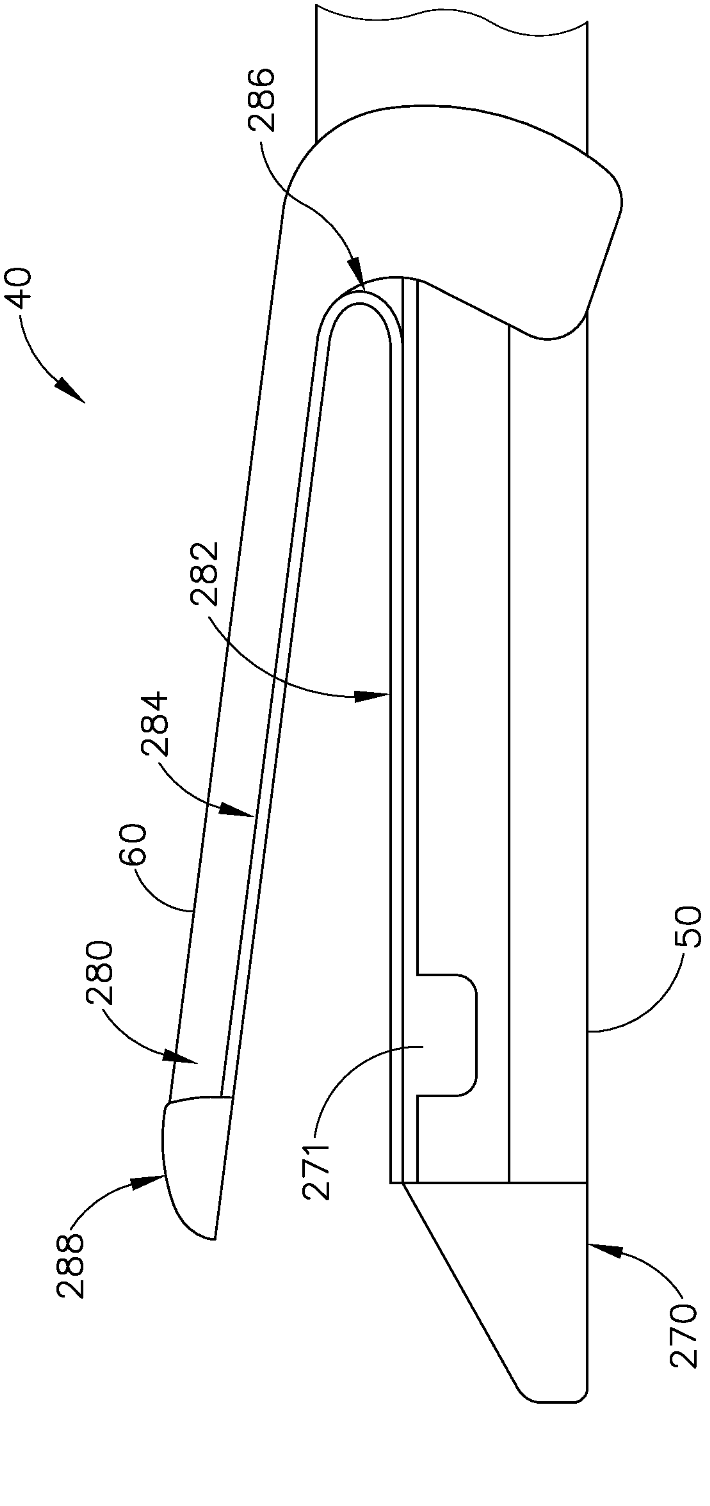
FIG. 14 depicts an elevational view of the end effector of FIG. 3 and the buttress of FIG. 13 disposed on and between an underside of the anvil and the exterior top surface of the staple cartridge.

FIGS. 13-14 show an exemplary alternative staple cartridge (270) that may be inserted into lower jaw (50) of end effector (40). Other than as set forth below, staple cartridge (270) of this example is substantially similar to staple cartridge (70) as described above. For instance, cartridge (270), like cartridge (70) comprises a cartridge body (271) and tray (not shown) secured to the underside of cartridge body (271). Similarly, the upper side of cartridge body (271) presents a deck (273), against which tissue may be compressed when anvil (60) is in a closed position.

Unlike cartridge (70), cartridge (270) equipped with a buttress (280) disposed on deck (273) of cartridge body (271). In the present example, buttress (280) comprises a strong yet flexible material configured to structurally support a staple line. In addition or in the alternative, buttress (280) may be comprised of a material including, for example, a hemostatic agent such as fibrin to assist in coagulating blood and reduce bleeding at the severed and/or stapled surgical site along tissue (90).

In other examples, buttress (280) may comprise materials other than those discussed above. For example, other adjuncts or hemostatic agents such as thrombin may be used such that buttress (280) may assist to coagulate blood and reduce the amount of bleeding at the surgical site. The hemostatic abilities of such adjuncts may also contribute to the use of such adjuncts as adhesives and sealants. The agents may assist to coagulate blood at a surgical site which allows tissue surrounding such blood to stick together and may prevent leaks along the stapled tissue site, for example. Other adjuncts or reagents that may be incorporated into buttress (280) may further include but are not limited to medical fluid or matrix components. By way of example only, buttress (280) may include natural or genetically engineered absorbable polymers or synthetic absorbable polymers, or mixtures thereof. Merely illustrative examples of natural or genetically engineered absorbable polymers are proteins, polysaccharides and combinations thereof. Merely illustrative examples of proteins that may be used include prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one). Other suitable compounds, materials, substances, etc., that may be used in a medical fluid or matrix will be apparent to those of ordinary skill in the art in view of the teachings herein.

Buttress (280) includes a cartridge portion (282), an anvil portion (284), and an intermediate portion (286) disposed between the proximal ends of cartridge portion (282) and anvil portion (284). Anvil portion (284) includes flap (288) that wraps over the distal end of anvil (60), as shown in FIG. 14. Flap (288), for example, defines a pocket (not shown) sized for receipt of the distal end of anvil (60), to thereby attach anvil portion (284) of buttress (280) to anvil (60). Intermediate portion (286) of buttress (280) may comprise a preformed bend to facilitate loading of cartridge (270) in lower jaw and insertion of anvil (60) in the pocket defined by flap (288).

Cartridge (270) further includes fasteners such as hooks (290) that grasp onto buttress (280). Hooks (290) and buttress (280) may provide a fastening relationship, such as a hook and loop fastening relationship in which hooks (290) connect to loops formed within the material of buttress (280). Although the present example is shown as having hooks (290), it should be understood that any other suitable means may be used to fasten cartridge portion (282) of buttress (280) to deck (273) of cartridge (270).

Figure 15:
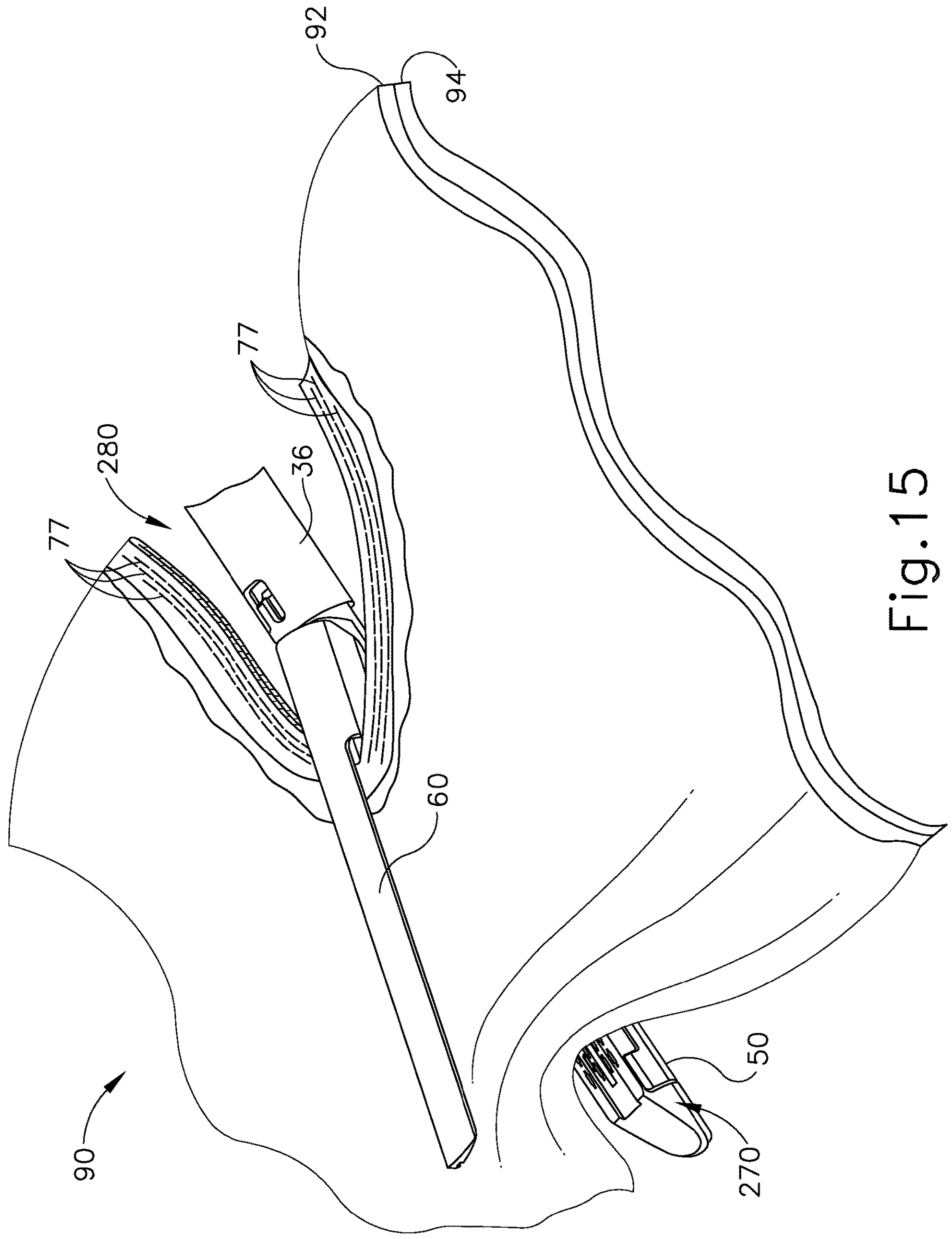
FIG. 15 depicts a perspective view of an end effector with the buttress of FIG. 13, the end effector having fired and released staples and the buttress of FIG. 13 into and onto the tissue.

In use, cartridge (270) with buttress (280) is removably received into lower jaw (50) of end effector (40), as shown in FIG. 13. When end effector (40) including cartridge (270) and buttress (280) is used, as shown in FIG. 15, staples (277) are driven into tissue (90) concurrently or slightly prior to firing beam (82) cutting through tissue (90) while also cutting through buttress (280). Staples (277) may capture portions of buttress (280) and drive those portions into tissue (90) or at least secure buttress (280) to tissue (90). Firing beam (82) slices through buttress (280) as it severs tissue (90) in use, applying material from buttress (280) onto severed tissue.

While buttress (280) is shown as having a certain configuration, it should be understood that the precise configuration of buttress (280) may be varied. For instance, in some versions, a medical fluid may be suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Exemplary gelling materials include proteins, polysaccharides, polynucleotides, and other materials such as alginate, cross-linked alginate, poly(N-isopropylacrylamide), poly (oxyalkylene), copolymers of poly(ethylene oxide)-poly (propylene oxide), poly(vinyl alcohol), polyacrylate, or monostearoyl glycerol co-Succinate/polyethylene glycol (MGSA/PEG) copolymers, and combinations of any of the foregoing.

Buttress (280) may alternatively comprise a fibrous pad, a foam, a mesh, or another structure capable of containing an adhesive or other type of medical fluid. By way of example only, cartridge (270) and/or buttress (280) may be constructed in accordance with the teachings of U.S. Patent Application Publication No. 2013/0068816, entitled SURGICAL INSTRUMENT AND BUTTRESS MATERIAL, published Mar. 21, 2013; U.S. Patent Application Publication No. 2013/0062391, entitled SURGICAL INSTRUMENT WITH FLUID FILLABLE BUTTRESS, published Mar. 14, 2013, now U.S. Pat. No. 9,999,408; U.S. Patent Application Publication No. 2013/0068820, entitled FIBRIN PAD MATRIX WITH SUSPENDED HEAT ACTIVATED BEADS OF ADHESIVE, published Mar. 21, 2013, now U.S. Pat. No. 8,814,025; U.S. Patent Application Publication No. 2013/0082086, entitled ATTACHMENT OF SURGICAL STAPLE BUTTRESS TO CARTRIDGE, published Apr. 4, 2013, now U.S. Pat. No. 8,899,464; U.S. Patent Application Publication No. 2013/0037596, entitled DEVICE FOR APPLYING ADJUNCT IN ENDOSCOPIC PROCEDURE, published Feb. 14, 2013, now U.S. Pat. No. 9,492,170; U.S. Patent Application Publication No. 2013/0062393, entitled RESISTIVE HEATED SURGICAL STAPLE CARTRIDGE WITH PHASE CHANGE SEALANT, published Mar. 14, 2013, now U.S. Pat. No. 8,998,060; U.S. Patent Application Publication No. 2013/0075446, entitled SURGICAL STAPLE ASSEMBLY WITH HEMOSTATIC FEATURE, published Mar. 28, 2013, now U.S. Pat. No. 9,393,018; U.S. Patent Application Publication No. 2013/0062394, entitled SURGICAL STAPLE CARTRIDGE WITH SELF-DISPENSING STAPLE BUTTRESS, published Mar. 14, 2013, now U.S. Pat. No. 9,101,359; U.S. Patent Application Publication No. 2013/0075445, entitled ANVIL CARTRIDGE FOR SURGICAL FASTENING DEVICE, published Mar. 28, 2013, now U.S. Pat. No. 9,198,644; and U.S. Patent Application Publication No. 2013/0075447, entitled ADJUNCT THERAPY FOR APPLYING HEMOSTATIC AGENT, published Mar. 28, 2013, the disclosure of which is incorporated by reference herein.

III. Exemplary Alternative Wedge Sleds

In some instances, it may be desirable to provide additional and/or alternative structures and for cutting tissue and/or buttresses (280). For instance, in some examples instrument (10) itself may be reusable while cartridge (70, 270) may be disposable. Because of this, repeated re-use of instrument (10) may cause cutting edge (84) of firing beam (82) to become dull. Such dulling may be intensified by the use of a cartridge (270) that includes a buttress (280) similar to those discussed above. In addition or in the alternative, cutting edge (84) and/or other portions of firing beam (82) may encounter a buildup of material that forms buttress (280) as the same firing beam (82) is fired through a plurality of buttresses (280). Such a buildup of material may adversely impact the ability of firing beam (82) to sever tissue and/or additional buttresses (280). In additional or in the alternative, such a buildup of material may provide increased friction or interference that requires additional force to drive firing beam (82) distally. Various examples of additional and/or alternative structures that may be used to provide at least some disposable cutting feature(s) are described in greater detail below, while other examples will be apparent to those of ordinary skill in the art in view of the teachings herein.

A. Exemplary Wedge Sled with Rotatable Blade

Figure 16:
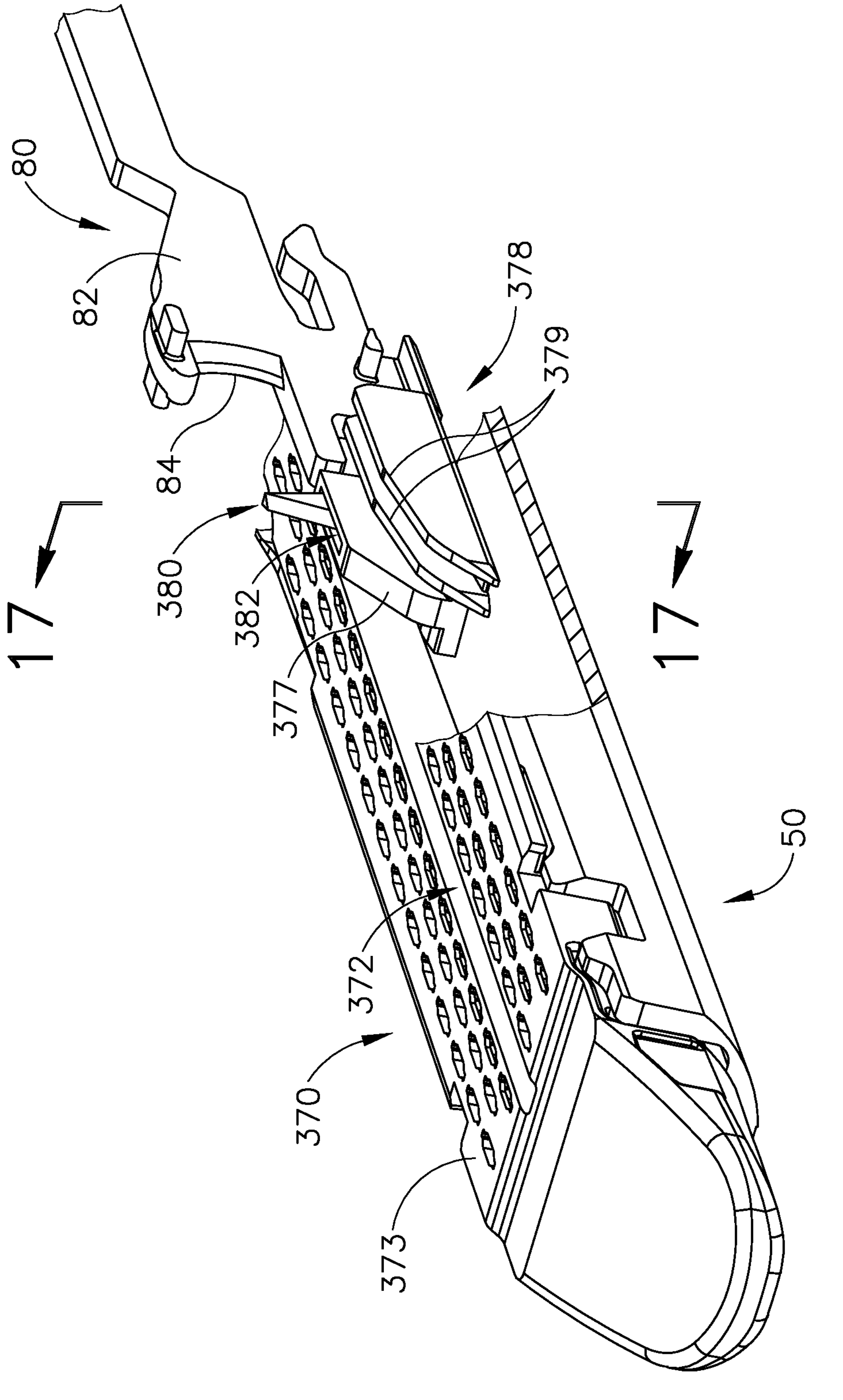
FIG. 16 depicts a partial perspective view of an exemplary variation of the end effector of FIG. 3, with a portion of the end effector cut away to reveal a wedge sled equipped with a rotatable secondary cutting blade.
Figure 17:
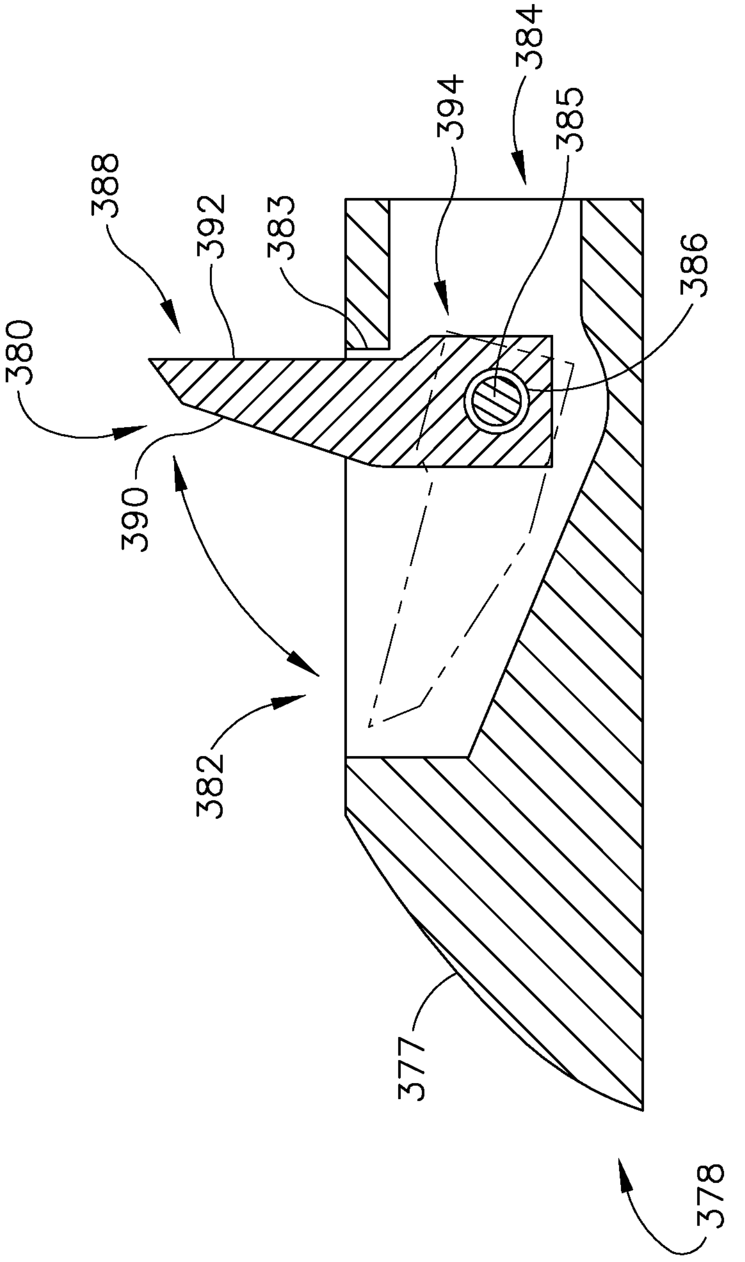
FIG. 17 depicts a cross-sectional view of the wedge sled of FIG. 16, taken along line 17-17 of FIG. 16, with the secondary cutting blade in an extended position.

FIG. 16 shows a perspective cutaway view of lower jaw (50) and an alternative staple cartridge (370). Staple cartridge (370) may be used as a substitute for staple cartridge (70). In addition, or in alternative, staple cartridge (370) may include a buttress (280) like staple cartridge (270) or any other kind of buttress, including but not limited to the various buttresses described in the various references cited herein. Staple cartridge (370) is substantially similar to staple cartridges (70, 270) described above with the primary difference being that staple cartridge (370) is equipped with an exemplary alternative wedge sled (378). Wedge sled (378) is similar to wedge sled (78) described above. In the present example, wedge sled (378) has been modified relative to wedge sled (78) to accommodate a secondary cutting blade (380) that is rotatable into wedge sled (378). In particular, as shown in FIGS. 16-17, wedge sled (378) includes a body (377) a plurality of cam surfaces (379). Body (377) defines a blade slot (382). Body and cam surfaces (379) are shorter relative to cam surface (79) of wedge sled (78), yet body (377) and cam surfaces (379) are oriented at an angle that is steeper than the angle of cam surface (79) of wedge sled (78). Accordingly, wedge sled (378) occupies the same amount of longitudinal space within cartridge (370) as wedge sled (78) in cartridge (70, 270), making wedge sled (378) substantially interchangeable with wedge sled (78). The angle of cam surfaces (379) permit wedge sled (378) to drive multiple staple drivers (75) upwardly simultaneously and/or in a certain predetermined sequence.

Blade slot (382) is configured to accommodate the rotation of blade (380) within wedge sled (378). As can best be seen in FIG. 17, blade slot (382) has a shape approximately corresponding to a shape defined by blade (380) rotating between a retracted position (shown in phantom) and an extended position. Additionally, blade slot (382) defines a stop feature (383) which, as will be described in greater detail below, prevents blade from rotating proximally beyond the extended position. The shape of blade slot (382) further defines a proximal opening (384) in wedge sled (378). As will be described in greater detail below, proximal opening provides access to blade (380) such that blade may be actuated by firing beam (82) from a retracted position to an extended position. In other examples, blade slot (382) may have any other suitable shape as will be apparent to those of ordinary skill in the art in view of the teachings herein.

As can be seen in FIG. 17, wedge sled (378) further comprises a rotation pin or shaft (385), which extends through blade slot (382). A through hole (386) in blade (380) permits blade (380) to pivotably couple to wedge sled (378) such that blade (380) can rotate distally to the retracted position. Although not shown in FIG. 17, it should be understood that rotation shaft (385) may be equipped with bushings, bearings, or other components or features suitable to aid rotation of blade (380). Additionally, rotation shaft (385) may be equipped with components or features such as springs suitable to resiliently bias blade (380) toward the retracted or extended position.

Blade (380) has a cross-sectional shape similar to a small knife. In particular, wither reference to blade (380) in the extended position, blade (380) has an upper cutting portion (388) and a lower attachment portion (394). Upper cutting portion (388) comprises a distally facing angular cutting edge (390) and a proximally facing flat portion (392). Cutting edge (390) extends at an angle upwardly from attachment portion (394). Although cutting edge (390) comprises a straight edge extending at an angle, it should be understood that cutting edge (390) may take on any other suitable shape. For instance, cutting edge (390) may be curved, serrated, saw toothed, and/or otherwise configured. Cutting edge (390) may further be angled differently relative to the angle shown.

Flat portion (392) extends upwardly from attachment portion (394). Like with cutting edge (390), flat portion (392) need not be limited to the shape described herein. As will be described in greater detail below, flat portion (392) provides a surface that may engage with stop feature (383) of wedge sled (378).

Upper cutting portion (388) of blade (380) extends upwardly to a certain height above wedge sled (378). In the present example, the height of upper cutting portion (388) is configured to cut through both a buttress (280) and tissue (90). In other examples, upper cutting portion (388) may have a height that is less than the height depicted such that upper cutting portion (388) only cuts through a buttress (280) immediately adjacent to cartridge (370), without necessarily cutting through tissue (90) that is positioned above buttress (280). It should be understood that upper cutting portion (388), or the other elements of cutting portion (388) described above, may be of any other suitable shape, height, or configuration as will be apparent to those of ordinary skill in the art in view of the teachings herein.

In an exemplary mode of operation, blade (380) is in the retracted position prior to insertion of cartridge (370) into lower jaw (50). In the retracted position, blade (380) is recessed entirely inside cartridge (370) and wedge sled (378). Accordingly, an operator is protected from inadvertent contact with blade (380) while inserting cartridge (70, 270) into lower jaw (50).

Once an operator has inserted cartridge (370) into lower jaw (50), blade (380) remains retracted until an operator initiates the firing sequence. Once the firing sequence is initiated, firing beam (82) is driven distally such that knife member (80) contacts wedge sled (378). Knife member (80) may include one or more protruding features (not shown) configured to engage blade (380) such that blade may be actuated into the extended position, with stop feature (383) arresting further rotation. Alternatively, wedge sled (378) may be equipped with features suitable to actuate blade (380) upon knife member (80) contacting wedge sled (378). In the extended position, blade (380) extends through a deck (373) of cartridge (370).

With blade (380) in the extended position, firing beam (82) continues to advance distally, driving cutting edge (390) of blade (380) through a buttress (280) (if equipped) and tissue (90). Cutting edge (84) of knife member (80) may trail shortly behind blade (380), such that cutting edge (84) cuts any tissue (90) or buttress (280) material left uncut by blade (380). It should be understood that cutting edge (84) of knife member (80) and cutting edge (390) of blade (380) follow a path that is substantially identical. Such a path may generally be defined by a longitudinally extending channel (372) of cartridge (370). By making the first cutting pass through buttress (280) (and in some versions, tissue (90) as well), blade (380) may reduce wear and/or buildup on knife member (80), thereby prolonging the useful life of knife member (80). Additionally, it should be understood that both blade (380) and knife member (80) trail cam surfaces (379) such that wedge sled (378) will drive staples (77) through a given region of tissue before that particular region of tissue is cut by blade (380) or knife member (80). The stapling and cutting action may still be considered substantially simultaneous at that region of tissue because wedge sled (378) is configured such that the difference in timing between stapling and cutting is substantially short.

Once instrument (10) has been fired, cartridge (370) may be removed along with blade (380) such that a new cartridge (370) and/or blade (380) may be inserted into lower jaw (50). It should be understood that cartridge (370) may be replaced with an identical cartridge (370) or a different cartridge (70, 270, 370). For instance, some cartridges (370) may be equipped with blades (380) configured for different procedures. By way of example only, cartridge (370) may include a sharper blade (380) for use with lung tissue. Alternatively, cartridge (370) may include a more robust blade (380) for use with stomach tissue. Of course, cartridge (370) may include a blade (380) suitable to cut through any tissue as will be apparent to those of ordinary skill in the art in view of the teachings herein.

B. Exemplary Wedge Sled with Fixed Blade

Figure 18:
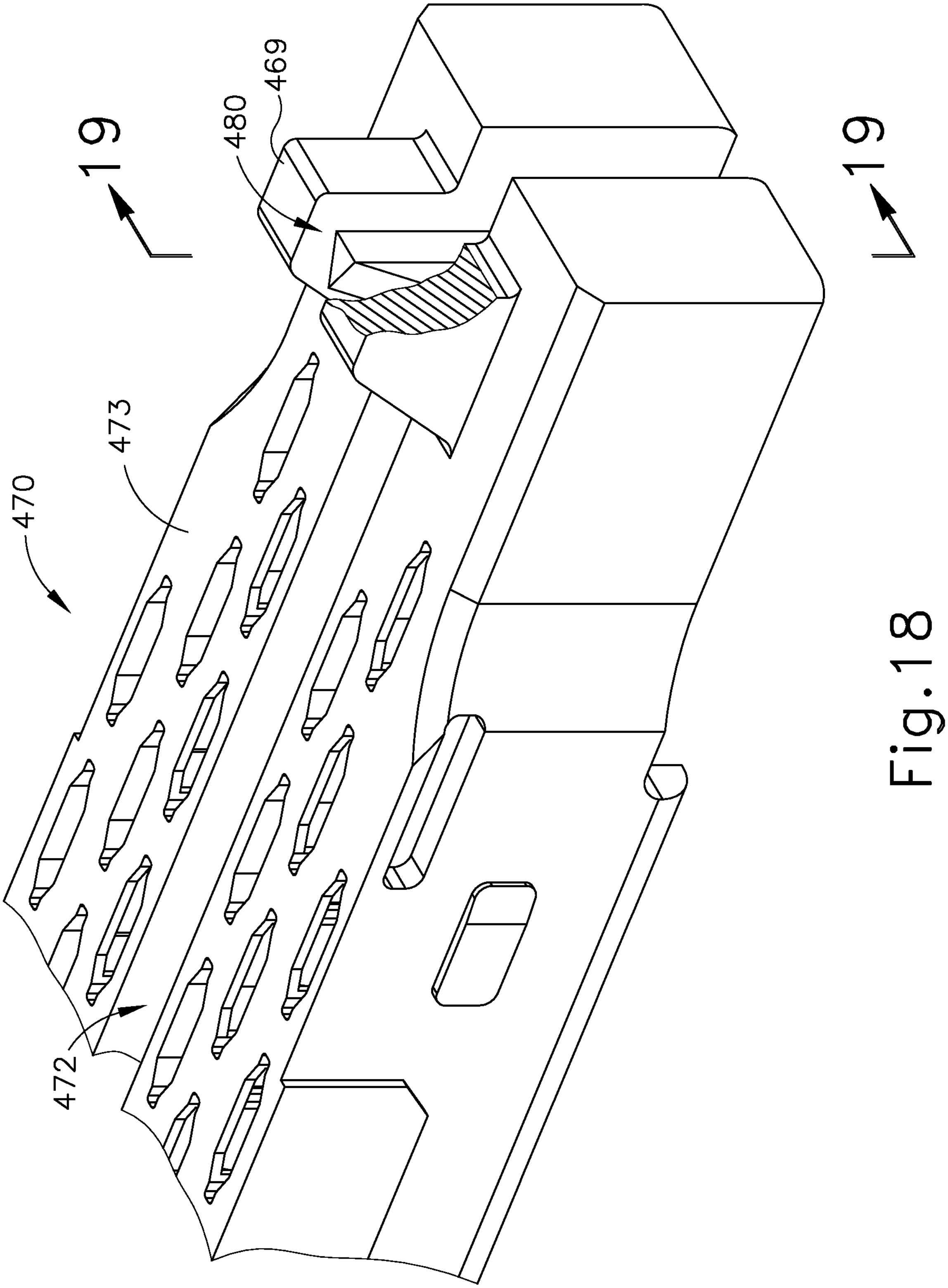
FIG. 18 depicts a partial perspective view of another exemplary variation of the end effector of FIG. 3, with a portion of the end effector cut away to reveal a wedge sled equipped with a fixed secondary cutting blade.

FIG. 18 shows a perspective cutaway view of another exemplary alternative staple cartridge (470) that is equipped with an exemplary alternative wedge sled (478). In the present example, cartridge (470) is substantially the same as cartridge (70, 270) described above, except cartridge (470) includes an upwardly projecting guard (469) that is unitarily coupled to a deck (473) of cartridge (470). Like cartridge (70, 270), cartridge (470) includes a longitudinally extending channel (472) in deck (473), which also extends through guard (469). As will be discussed in greater detail below, guard (469) is configured to cover a blade (480), which is fixedly attached to wedge sled (478).

Wedge sled (478) is similar to wedge sled (78, 378) described above. In the present example, like wedge sled (378), wedge sled (478) has been modified relative to wedge sled (78) to accommodate a secondary cutting blade (480)

that is fixedly secured to wedge sled (478). In particular, as can best be seen in FIG. 19, wedge sled (478) includes a body (477) that defines a blade slot (482). Body (477) may also include a plurality of cam surfaces (not shown) suitable to drive staples (77), via staple drivers, into tissue. Body (477) is shorter relative to cam surface (79) of wedge sled (78), yet body (477) and cam surfaces are oriented at an angle that is steeper than the angle of cam surface (79) of wedge sled (78). Accordingly, wedge sled (478) occupies the same amount of space longitudinally within cartridge (470) as wedge sled (78), making wedge sled (478) substantially interchangeable with wedge sled (78). The angle of wedge sled (478) permit wedge sled (478) to drive multiple staple drivers (not shown) upwardly simultaneously and/or in a certain predetermined sequence.

Blade slot (482) is configured to accommodate the blade (480) within wedge sled (478). As can best be seen in FIG. 19, blade slot (482) has a shape approximately corresponding to a shape defined by a lower region of blade (480). Unlike blade (380) of wedge sled (378), blade (480) of wedge sled (478) is fixed relative to wedge sled (478). Thus, blade slot (482) does not need to be configured to accommodate rotation or pivoting of blade (480). In other examples, blade slot (482) may have any other suitable shape as will be apparent to those of ordinary skill in the art in view of the teachings herein.

Figure 19:
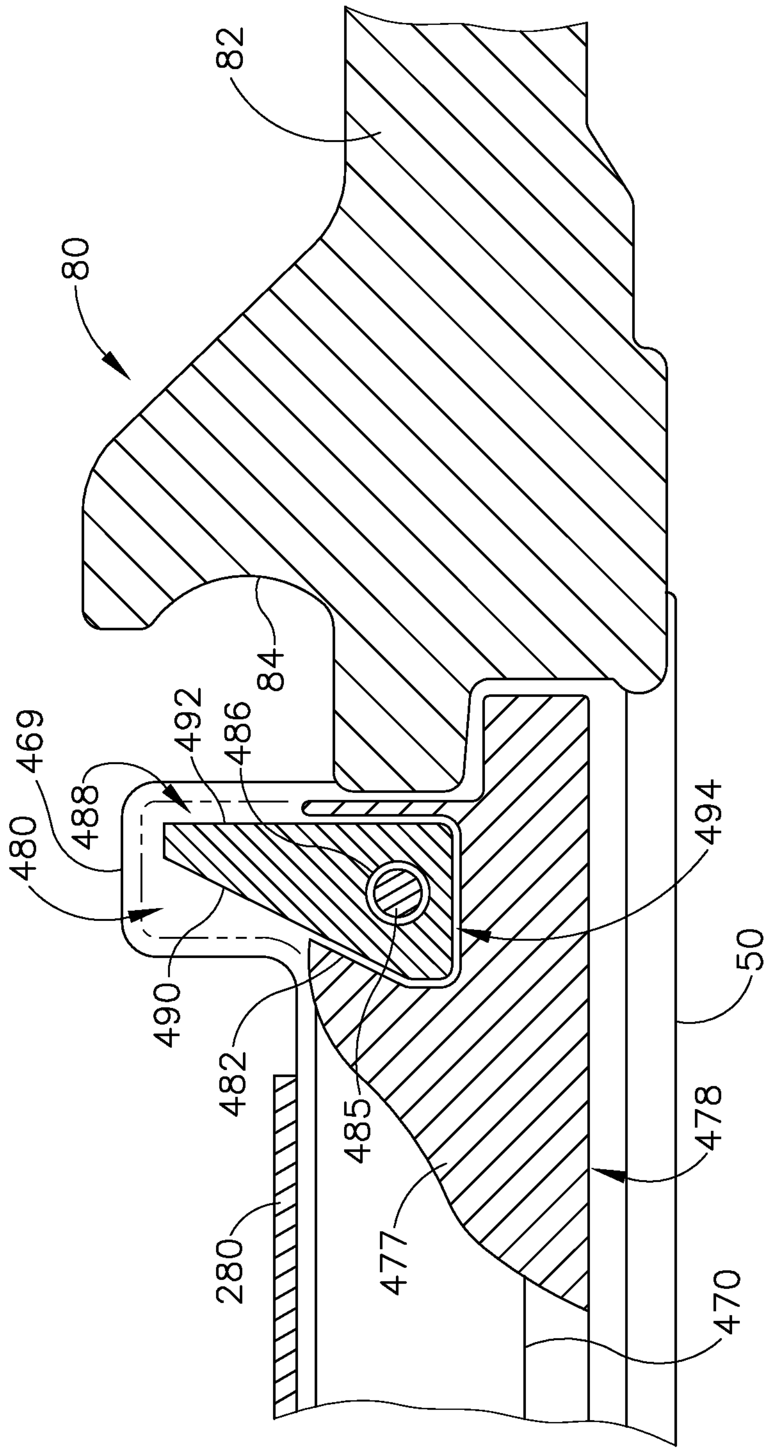
FIG. 19 depicts a side cross-sectional view of the wedge sled of FIG. 18, taken along line 19-19 of FIG. 18, with the wedge sled in a proximal position.

As can be seen in FIG. 19, wedge sled (478) further comprises a pin or shaft (485), which extends through blade slot (482). A through hole (486) in blade (480) permits blade (480) to be fixedly secured to wedge sled (478) such that blade (480) is substantially fixed relative to wedge sled (478).

Blade (480) has a cross-sectional shape similar to blade (380). In particular, blade (480) has an upper cutting portion (488) and a lower attachment portion (494). Upper cutting portion (488) comprises a distally facing angular cutting edge (490) and a proximally facing flat portion (492). Cutting edge (490) extends at an angle upwardly from attachment portion (494). Like with cutting edge (390) and flat portion (394) described above, cutting edge (490) and flat portion (494) may comprise any suitable alternative configuration as will be apparent to those of ordinary skill in the art in view of the teachings herein.

Upper cutting portion (488) of blade (480) extends upwardly to a certain height above wedge sled (478). In the present example, the height of upper cutting portion (488) is configured to cut through both a buttress (280) and tissue (90). Although, like with upper cutting portion (388) described above, the height of upper cutting portion (488) may be varied to cut through any desired combination of buttress (280) and/or tissue (90) as will be apparent to those of ordinary skill in the art in view of the teachings herein.

In an exemplary mode of operation, and as shown in FIG. 19, blade (480) is retracted into guard (469) prior to insertion of cartridge (470) into lower jaw (50). When blade (480) is retracted into guard (469), blade (480) is entirely inside cartridge (470). Accordingly, an operator is protected from inadvertent contact with blade (480) while the operator handles cartridge (470) and inserts cartridge (470) into lower jaw (50). Additionally, guard (469) may prevent premature contact between tissue and blade (480) during closure of anvil (60) toward deck (473), until a firing sequence is initiated (e.g., until knife member (80) is advanced distally). For instance, in absence of guard (469), the closing action of anvil (60) may tend to drive tissue proximally toward blade (480) when anvil (60) compresses tissue against deck (473). If such a proximal "milking" action of tissue occurs, guard (469) blocks the proximally driven tissue from engaging blade (480).

Figure 20:
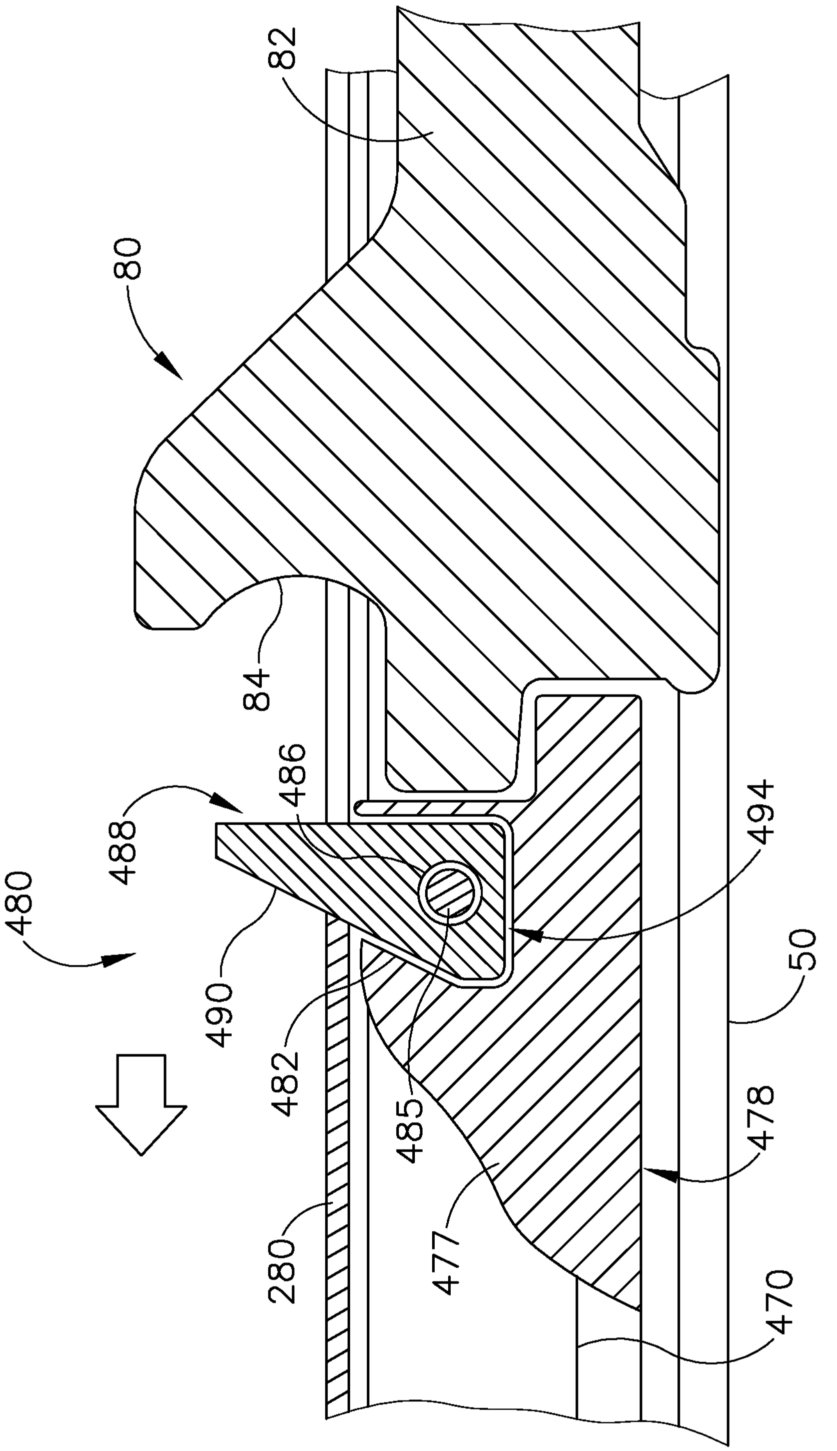
FIG. 20 depicts a side cross-sectional view of the wedge sled of FIG. 18, taken along line 19-19 of FIG. 18, with the wedge sled in a distal position.

Once an operator has inserted cartridge (470) into lower jaw (50), blade (480) remains retracted until an operator initiates the firing sequence. Once the firing sequence is initiated, firing beam (82) is driven distally to contact wedge sled (478). As shown in FIG. 20, firing beam (82) continues to advance distally, driving wedge sled (478) distally and thereby driving blade (480) out of guard (469), such that cutting edge (490) of blade (480) may cut through a buttress (280) (if equipped) and tissue (90). Cutting edge (84) of knife member (80) may trail shortly behind blade (480), such that cutting edge (84) cuts any tissue (90) or buttress (280) material left uncut by blade (480). It should be understood that cutting edge (84) of knife member (80) and cutting edge (490) of blade (480) follow a path that is substantially identical. Such a path may generally be defined by longitudinally extending channel (470) of cartridge (770). By making the first cutting pass through buttress (280) (and in some versions, tissue (90) as well), blade (480) may reduce wear and/or buildup on knife member (80), thereby prolonging the useful life of knife member (80). Additionally, it should be understood that both blade (480) and knife member (80) trail cam surfaces (479) such that wedge sled (478) will drive staples (77) through a given region of tissue before that particular region of tissue is cut by blade (480) or knife member (80). The stapling and cutting action may still be considered substantially simultaneous at that region of tissue because wedge sled (478) is configured such that the difference in timing between stapling and cutting is substantially short.

Once instrument (10) has been fired, cartridge (470) may be removed along with blade (480) such that a new cartridge (70, 370, 470) and/or blade (480) may be inserted into lower jaw (50). It should be understood that cartridge (470) may be replaced with an identical cartridge (470) or a different cartridge (70, 270, 370). For instance, like with cartridge (370) discussed above, some cartridges (470) may be equipped with blades (480) configured for different procedures such as those described above.

Figure 21:
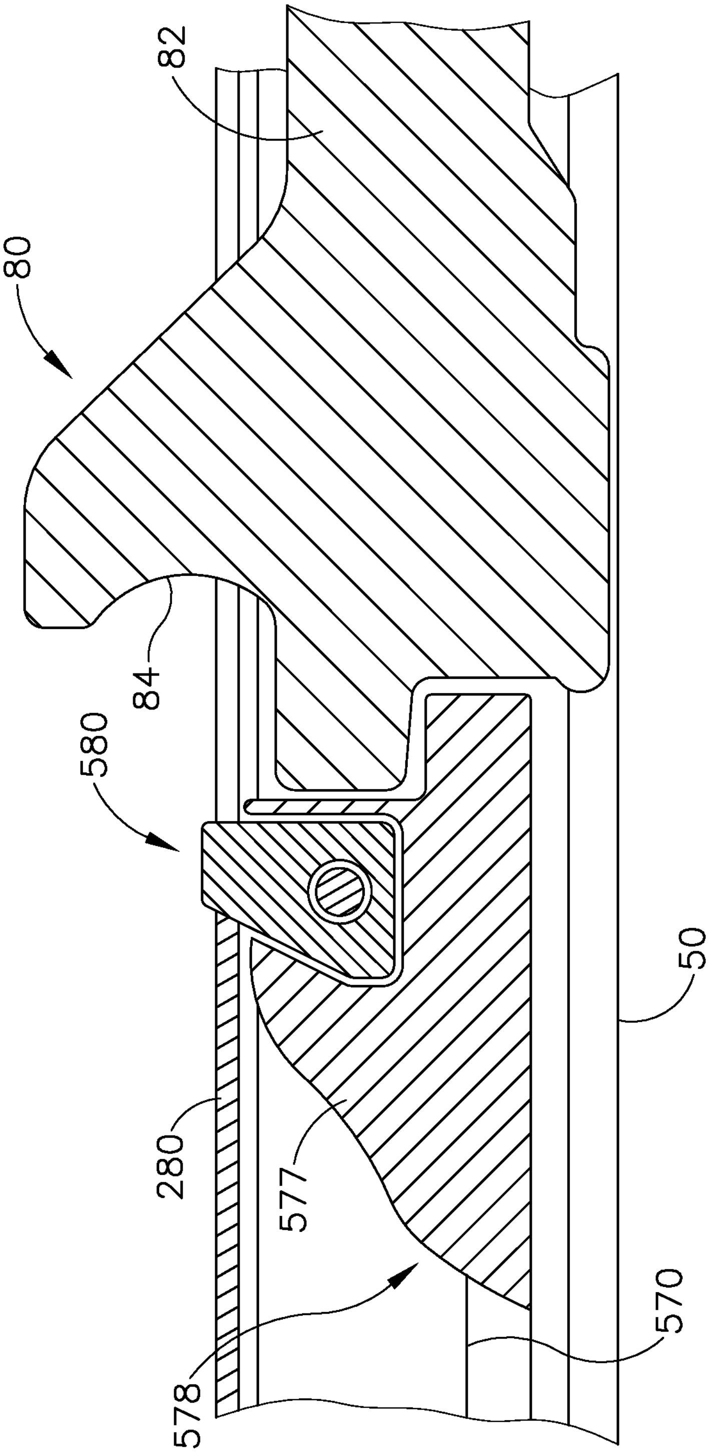
FIG. 21 depicts a side cross-sectional view of an exemplary variation of the wedge sled of FIG. 18.

FIG. 21, shows an alternative wedge sled (578) that may be used with cartridge (70, 270, 470). Wedge sled (578) is functionally and structurally the same as wedge sled (478) discussed above, unless otherwise noted below. Unlike wedge sled (478), wedge sled (578) comprises a different secondary cutting blade (580). In particular, blade (580) is shorter relative to blade (480) such that blade (580) is configured to cut through only buttress (280) material, without also reaching tissue (90) positioned above buttress (280).

In some circumstances, buttress (280) material may be of a different thickness than the particular thickness depicted. Accordingly, it should be understood that cutting blade (580) is not limited to only cutting buttress (280) or cutting through all of buttress (280). Indeed, in some circumstances blade (580) may incidentally cut a portion of tissue (90). Yet in other circumstances, blade (580) may cut through only a portion of buttress (280), leaving the remaining buttress (280) material for cutting by cutting edge (84) of knife member (80).

C. Exemplary Wedge Sled with Biased Secondary Blade

Figure 22:
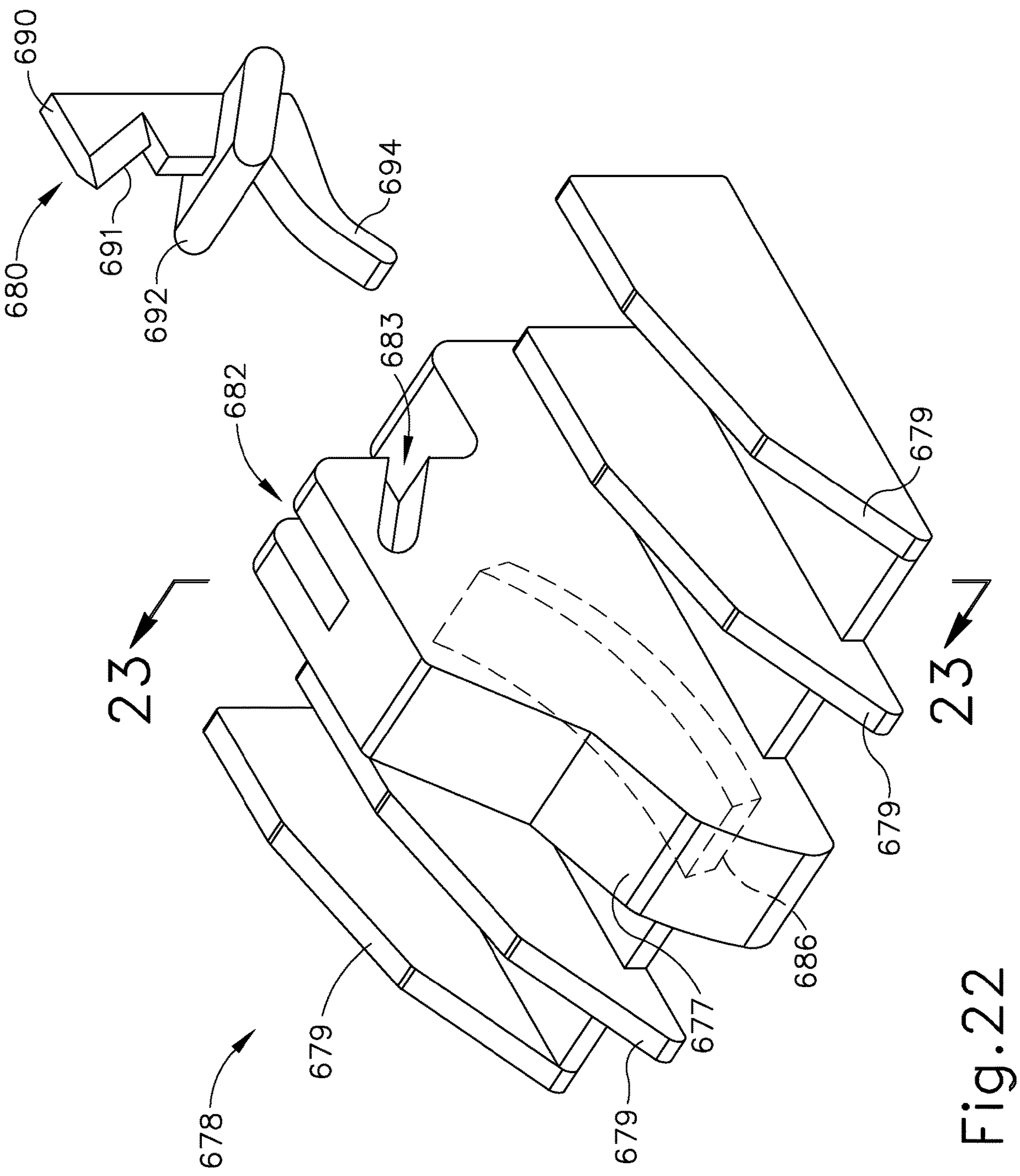
FIG. 22 depicts a perspective view of another exemplary wedge sled for use with the end effector of FIG. 3, the wedge sled having a upwardly translatable secondary cutting blade.

FIG. 22 shows a perspective view of another exemplary alternative wedge sled (678) that may be used with cartridge (670), which is a modified version of cartridge (70, 270). In many respects, wedge sled (678) of this example is similar to wedge sled (78, 378, 478, 578) described above. In the present example, like wedge sled (378, 478, 578), wedge sled (678) has been modified relative to wedge sled (78) to accommodate a secondary cutting blade (680). In particular, as can best be seen in FIG. 23, wedge sled (678) includes a body (677) and a plurality of cam surfaces (679). Body (677) defines a blade slot (682), which is configured to accommodate a blade (680), as will be described in greater detail below. Body (677) and cam surfaces (679) are shorter relative to cam surface (79) of wedge sled (78), yet cam surfaces (679) are oriented at an angle that is steeper than the angle of cam surface (79) of wedge sled (78). Accordingly, wedge sled (678) occupies the same amount of space longitudinally within cartridge (70, 270) as wedge sled (78), making wedge sled (678) substantially interchangeable with wedge sled (78). The angle of cam surfaces (679) permit wedge sled (678) to drive multiple staple drivers (not shown) upwardly simultaneously and/or in a certain predetermined sequence.

Blade slot (682) is configured to accommodate blade (680) within wedge sled (678). As can best be seen in FIG. 23, blade slot (682) comprises a translation slot (683) and an actuation cavity (684). Translation slot (683) corresponds to a translation sled (692) of blade (680). As will be described in greater detail below, translation sled (692) is configured to cooperate with knife member (80) to translate blade (680) from a retracted position to an extended position via translation slot (683).

Actuation cavity (684) defines a space for certain components of blade (680) (described below) and a resilient member (686) of wedge sled (678). Resilient member (686) comprises a leaf spring that extends proximally from a distal fixation feature (688) that is of unitary construction with wedge sled (678). As will be described in greater detail below, resilient member (686) is operable to flex up and down within actuation cavity (684) to resiliently bias blade (680) toward the retracted position. Accordingly, actuation cavity (684) is at least partially defined by the range of flexing motion of resilient member (686). Although actuation cavity (684) is shown as having a specific shape, it should be understood that the shape of actuation cavity (684) may be varied according to the shape and range of motion of resilient member (686). Additionally or in the alternative, as will be understood from the description below, the shape of actuation cavity (684) may also be varied according to the shape or translation path of blade (680).

Blade (680) comprises an upper cutting portion (690), translation sled (692), and a retaining feature (694). Cutting portion (690) comprises a sharp distally oriented cutting edge (691), which is configured to cut through buttress (280) and/or tissue (90). Like with cutting edge (390, 490) described above, cutting edge (691) may have a variety of alternative configurations that may be configured to cut through a variety of materials.

Translation sled (692) is of unitary construction with blade (680) and extends outwardly from blade (680). In other examples, translation sled (692) may be a separate from, and fixedly secured to blade (680). Translation sled (692) is generally integral with blade (680) and extends distally and outwardly from the front, right and left sides of blade (680). As can best be seen in FIG. 22, translation sled (692) is generally rectangular in shape with rounded distal and proximal ends. The longitudinal portion of the rectangular shape of translation sled (692) generally defines a plane which is oriented at an oblique angle relative to the longitudinal axis of cartridge (670). As will be described in greater detail below, translation sled (692) is slidably disposed in translation slot (683) that is formed in the body of wedge sled (680). Translation slot (683) provides a cam surface for translation sled (692), such that translation slot (693) and translation sled (692) provide upward movement of blade (680) relative to wedge sled (678) when blade (680) is driven distally relative to wedge sled (678). Although translation sled (692) is shown as being oriented at a specific angle relative to blade (680), it should be understood that translation sled (692) may be oriented at any suitable angle as will be apparent to those of ordinary skill in the art in view of the teachings herein.

Retaining feature (694) extends distally from blade (680). In particular, retaining feature (694) initially extends substantially perpendicular to a longitudinal axis of blade (680). As retaining feature (694) extends distally, retaining feature (694) curves downwardly at an angle. As will be understood, the shape of retaining feature (694) is configured to engage resilient member (686) to resiliently bias blade (680) toward the retracted position. Thus, retaining feature (694) may take on a variety of alternative shapes depending on the particular relationship between wedge sled (678) and blade (680) and other sub components thereof.

Unlike blade (380, 480, 580) of wedge sled (378, 478, 578), blade (680) of wedge sled (678) is configured to translate obliquely relative to wedge sled (478). In particular, translation slot (683) of wedge sled (678) is configured to mate with translation sled (692) of blade (680). Translation slot (683) and translation sled (692) are both oriented at an angle such that translation slot (683) and translation sled (692) are operable to cooperatively translate blade (680) upwardly as blade (680) is advanced distally. Thus, translation slot (683) and translation sled (692) are operable to transition blade (680) from the retracted position to the extended position when blade (680) is advanced distally.

Figure 23:
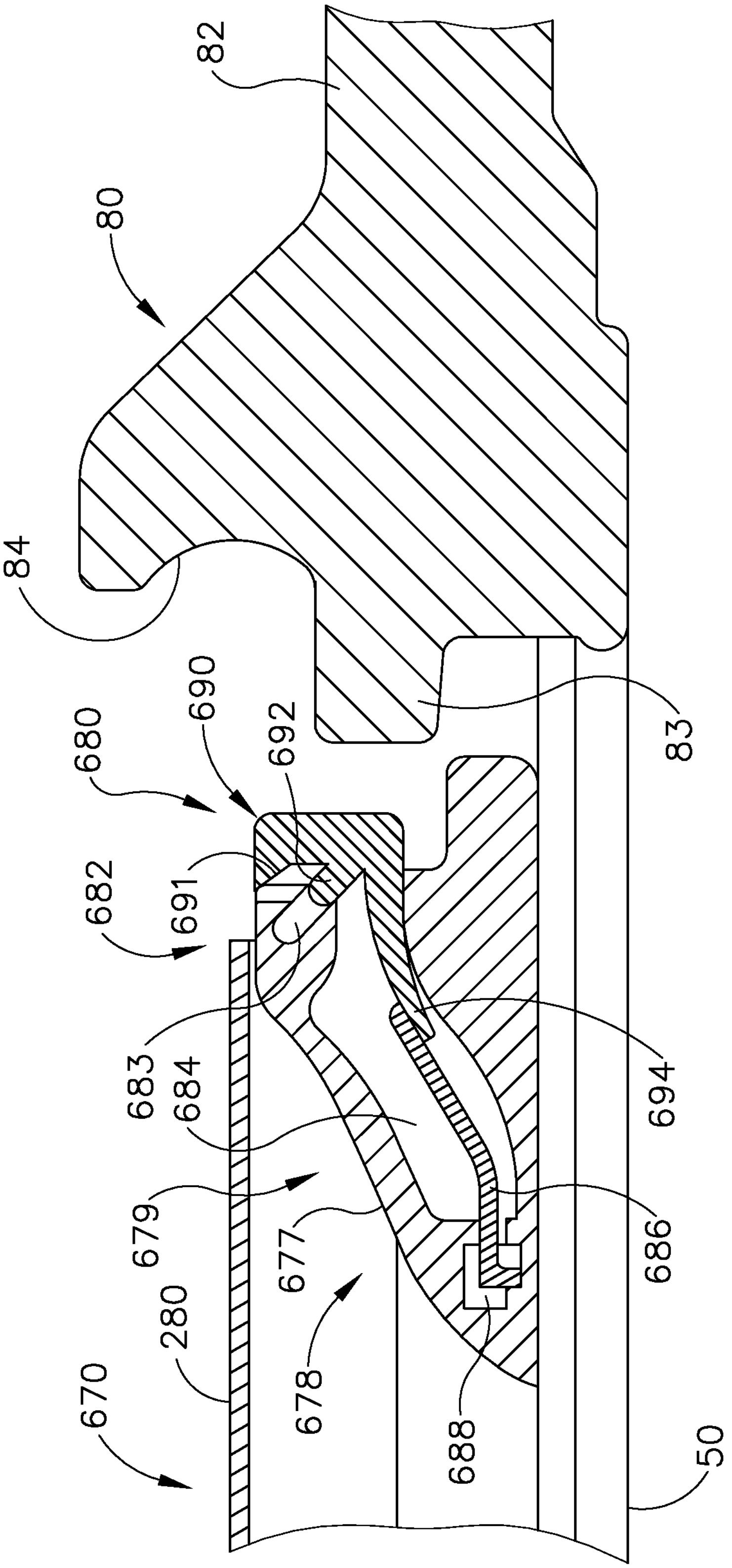
FIG. 23 depicts a side cross-sectional view of the wedge sled of FIG. 22, taken along line 23-23 of FIG. 22, with the secondary cutting blade in a retracted position.

As can best be seen in FIG. 23, resilient member (686) of wedge sled (678) and retaining feature (694) of blade (680) are configured to engage each other such that resilient member (686) exerts a force having a downward component and a proximal component on retaining feature (694). This force causes translation sled (692) of blade (680) to be biased toward the proximal end of translation slot (683) of wedge sled (678), thus resiliently biasing blade (680) toward the retracted position. In some versions, the distal edge of distal projection (83) is oriented at an angle between 75 degrees and 90 degrees relative to a horizontal plane. Such an angle may provide a camming action that assists in overcoming the bias of resilient member (686) to retract blade (680) proximally.

In an exemplary mode of operation, blade (680) is retracted initially in the retracted position for insertion of cartridge (670) into lower jaw (50). When blade (680) is in the retracted position, blade (680) is entirely inside cartridge (670). Accordingly, an operator is protected from inadvertent contact with blade (680) while inserting cartridge (670) into lower jaw (50).

Figure 24:
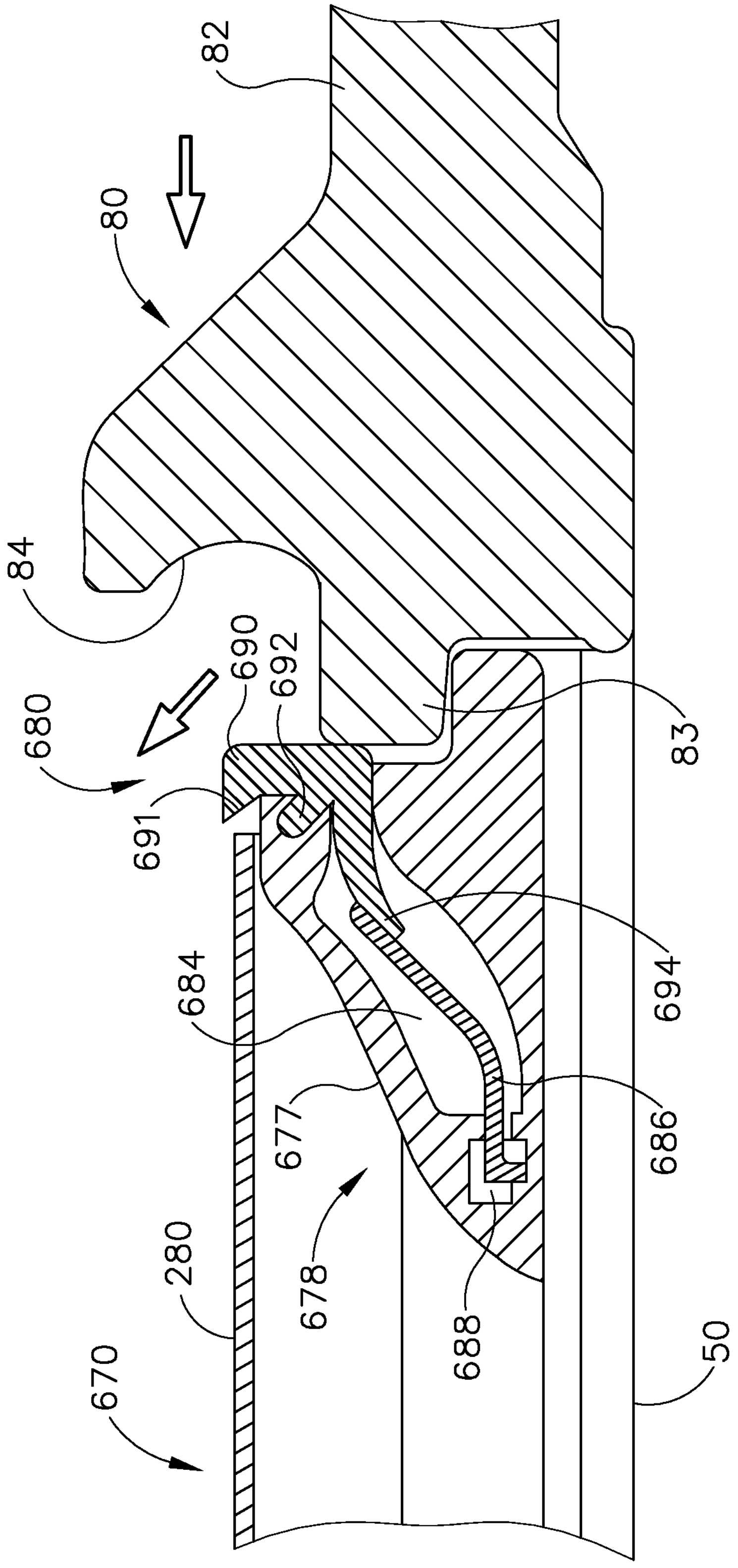
FIG. 24 depicts a side cross-sectional view of the wedge sled of FIG. 22, taken along line 23-23 of FIG. 22, with the secondary cutting blade in an extended position.

Once an operator has inserted cartridge (670) into lower jaw (50), blade (680) remains retracted until an operator initiates the firing sequence. Once the firing sequence is initiated, firing beam (82) is driven distally such that knife member (80) contacts blade (680) to first actuate blade (680) into the extended position and then to drive blade (680) and wedge sled (678) proximally. As shown in FIGS. 23-24, knife member (80) comprises a distal projection (83) which is configured to contact blade (680). Thus, as firing beam (82) is driven distally, blade (680) is correspondingly driven distally relative to wedge sled (678) by distal projection (83) of knife member (80). As blade (680) is driven distally, translation slot (683) of wedge sled (678) and translation sled (692) of blade (680) simultaneously and cooperatively drive blade (680) upwardly into the extended position, as can be seen in the transition from the state shown in FIG. 23 to the state shown in FIG. 24. It should be understood that, because blade (680) is resiliently biased toward the retracted position, blade (680) is only extended when acted upon by knife member (80). Continued advancement of firing beam (82) advances wedge sled (678) distally and drives cutting edge (691) of blade (680) through buttress (280) and/or tissue (90). Cutting edge (84) of knife member (80) may trail shortly behind blade (680), such that cutting edge (84) cuts any tissue (90) or buttress (280) material left uncut by blade (680).

It should be understood that cutting edge (84) of knife member (80) and cutting edge (690) of blade (680) follow a path that is substantially identical. Such a path may generally be defined by longitudinally extending channel (not shown) of cartridge (670). By making the first cutting pass through buttress (280) (and in some versions, tissue (90) as well), blade (680) may reduce wear and/or buildup on knife member (80), thereby prolonging the useful life of knife member (80). Additionally, it should be understood that both blade (680) and knife member (80) trail cam surfaces (379) such that wedge sled (678) will drive staples (77) through a given region of tissue before that particular region of tissue is cut by blade (680) or knife member (80). The stapling and cutting action may still be considered substantially simultaneous at that region of tissue because wedge sled (678) is configured such that the difference in timing between stapling and cutting is substantially short.

Once instrument (10) has been fired, knife member (80) may be retracted proximally. Proximal retraction of knife member (80) permits resilient member (686) to drive blade (680) back to the retracted position. Blade (680) is thus retracted in a spent cartridge (670), protecting the operator from inadvertent contact with cutting edge (691) when operator removes the spent cartridge (670) to replace spent cartridge (670) or to otherwise dispose of the spent cartridge (670). Cartridge (670) may be removed along with blade (680) such that a new cartridge (70, 270, 370, 470, 570), equipped with blade (380, 480, 580, 680), may be inserted into lower jaw (50). It should be understood that cartridge (670) may be replaced with an identical cartridge (670) or a different cartridge (70, 270, 370, 470, 570). For instance, like with wedge sled (378, 478, 578) discussed above, some cartridges (70, 270, 370, 470, 570) may be equipped with blades (680) configured for different procedures such as those described above.

D. Exemplary Wedge Sled with Translatable Blade

Figure 25:
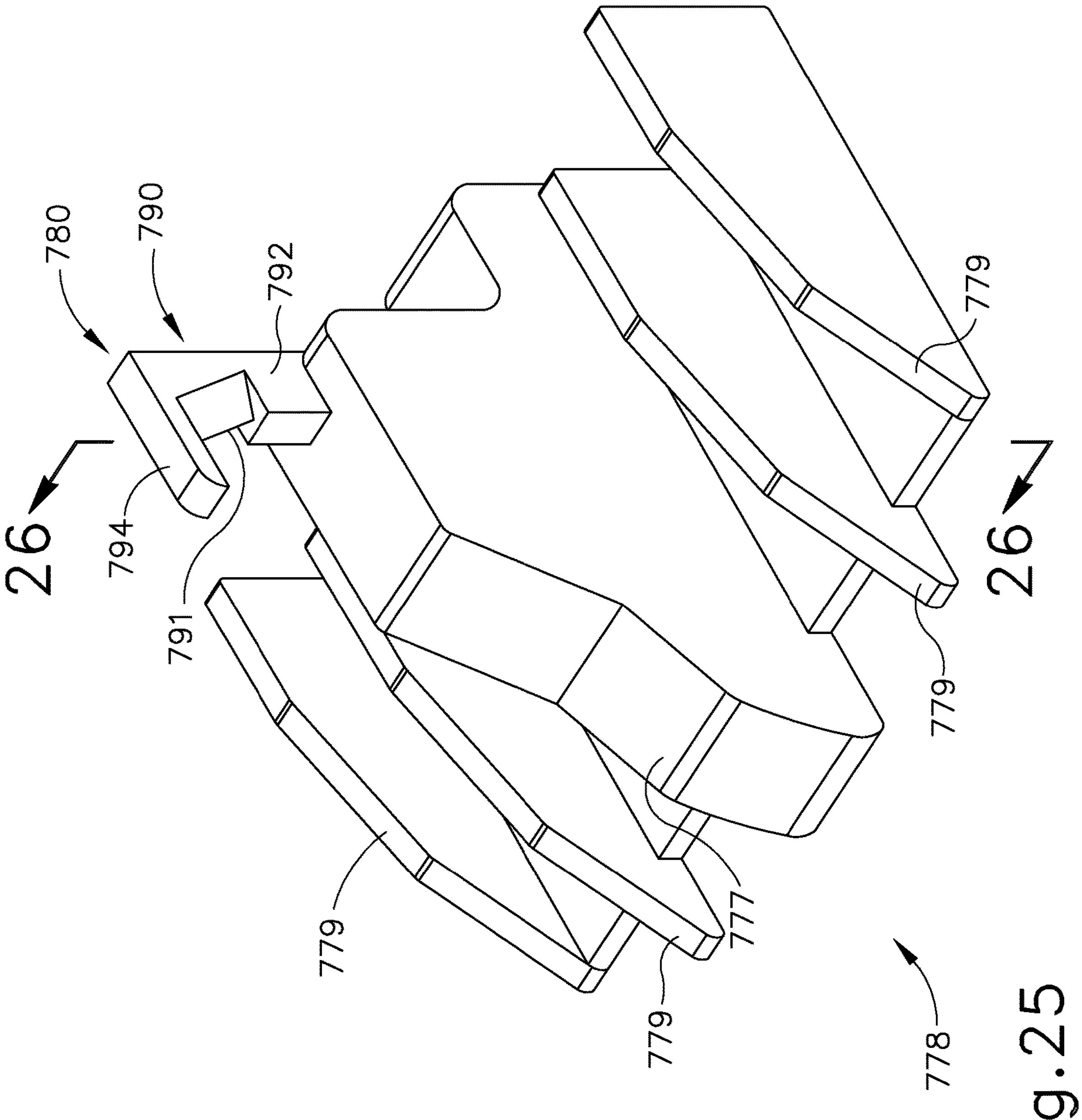
FIG. 25 depicts a perspective view of another exemplary wedge sled for use with the end effector of FIG. 3, the wedge sled having a fixed secondary cutting blade with a stabilizing nose.
Figure 26:
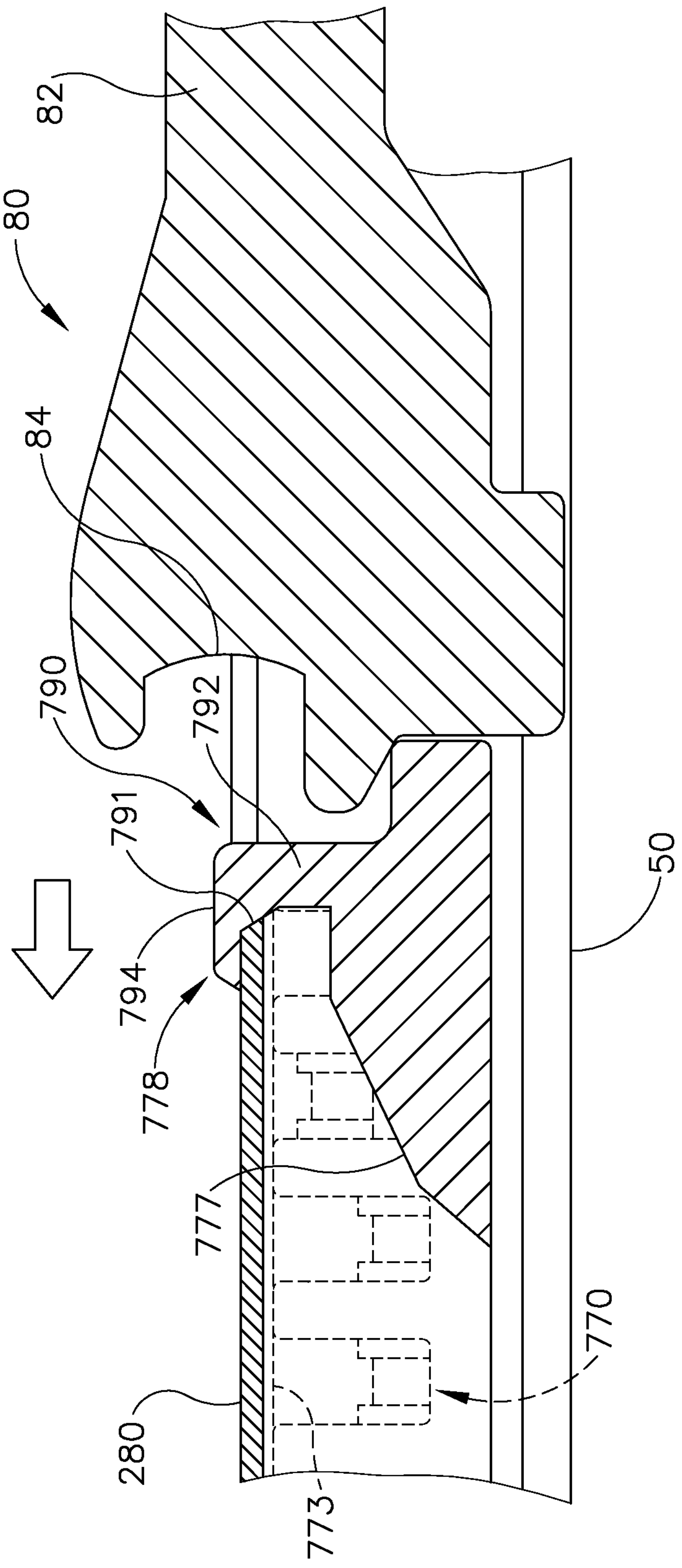
FIG. 26 depicts a side cross-sectional view of the wedge sled of FIG. 25 taken along line 26-26 of FIG. 25, with the secondary cutting blade advanced distally.

FIGS. 25-26 show another exemplary alternative wedge sled (778) for use with cartridge (770), which is a modified version of cartridge (70, 270). In many respects, wedge sled (778) of this example is similar to wedge sled (78, 378, 478, 578, 678) described above. Like wedge sled (378, 478, 578, 678), wedge sled (778) has been modified relative to wedge sled (78) to include an integral secondary cutting blade (780). In particular, as can best be seen in FIG. 25, wedge sled (778) includes a body (777) and a cam surface (779). Body (777) and cam surface (779) are shorter relative to cam surface (79) of wedge sled (78), yet cam surface (779) is oriented at an angle that is steeper than the angle of cam surface (79) of wedge sled (78). Accordingly, wedge sled (778) occupies the same amount of space longitudinally within cartridge (70, 270) as wedge sled (78), making wedge sled (778) substantially interchangeable with wedge sled (78). The angle of cam surfaces (779) permit wedge sled (778) to drive multiple staple drivers (75) upwardly simultaneously and/or in a certain predetermined sequence.

Blade (780) comprises an upper cutting portion (790), a body portion (792), and a stabilizing member (794). Cutting portion (790) comprises a sharp, distally oriented cutting edge (791), which is configured to cut through buttress (280) and/or tissue (90). Like with cutting edge (390, 490, 590, 691) described above, cutting edge (791) may have a variety of alternative configurations that may be configured to cut through a variety of materials.

Body portion (792) unitary couples blade (780) with wedge sled (778). In other words, wedge sled (778) and blade (780) comprise a single unitary component in this example. In other examples, blade (780) may be separate from, and fixedly secured to, wedge sled (778). Body portion (792) is sized to raise cutting portion (790) to height suitable for cutting buttress (280). While body portion (792) is shown as having a particular height, it should be understood that the height of body portion (792) may be varied according to a number of factors such as the height of deck (773), buttress (280) thickness, etc.

Stabilizing member (794) is positioned above cutting edge (791) and extends distally from blade (780). As can best be seen in FIG. 26, stabilizing member (794) is positioned to align with a top surface of buttress (280). Accordingly, stabilizing member (794) is operable to direct buttress (280) toward cutting edge (791), and may further assist in preventing buttress (280) from separating from deck (773) in the region adjacent to blade (780), as will be described in greater detail below. Additionally, stabilizing member (794) acts as a guard to prevent inadvertent operator contact with cutting edge (791). Although stabilizing member (794) is shown as having a generally rectangular shape extending a particular distance, it should be understood that stabilizing member (794) may have any suitable size or shape. For instance, in other examples stabilizing member (794) may extend distally further than depicted. Yet in other examples, stabilizing member (794) may taper outwardly or inwardly to a width that is wider or narrower than blade (780), respectively. Of course, stabilizing member (794) may comprise any other suitable configuration, size, and/or shape as will be apparent to those of ordinary skill in the art in view of the teachings herein.

In an exemplary mode of operation, blade (780) initially protrudes out of cartridge (70, 270) at the proximal end of cartridge (70, 270). Stabilizing member (794) is configured to protect an operator from inadvertent contact with cutting edge (791) while cartridge (70, 270) is inserted into lower jaw (50). Accordingly, an operator is protected from inadvertent contact with blade (780) even though blade (780) projects outwardly from cartridge (70, 270).

Once a user has inserted cartridge (70, 270) into lower jaw (50), the firing sequence may be initiated. Once the firing sequence is initiated, firing beam (82) is driven distally such that knife member (80) contacts wedge sled (778). As shown in FIG. 26, knife member (80) contacts wedge sled (778) and begins to drive wedge sled (778) and blade (780) distally. As blade (780) is driven distally, stabilizing member (794) of wedge sled (778) rides on the upper surface of buttress (280) to stabilize the cutting process. It should be understood that, since stabilizing member (794) rides on top of buttress (280), blade (780) only cuts buttress (280). In other examples, cutting edge (791) of blade (780) may be configured to be vertically higher. In some such examples, stabilizing member (794) may ride on tissue (90) or a buttress (280) that is adjacent to anvil (60). Thus, in other examples, blade (780) may be configured to cut other materials besides buttress (280) such as tissue (90) or other additional buttresses (280). Cutting edge (84) of knife member (80) may trail shortly behind blade (780), such that cutting edge (84) cuts any tissue (90) or buttress (280) material left uncut by blade (780).

It should be understood that cutting edge (84) of knife member (80) and cutting edge (790) of blade (780) follow a path that is substantially identical. Such a path may generally be defined by longitudinally extending channel (not shown) of cartridge (770). By making the first cutting pass through buttress (280) (and in some versions, tissue (90) as well), blade (780) may reduce wear and/or buildup on knife member (80) thereby prolonging the useful life of knife member (80). Additionally, it should be understood that both blade (780) and knife member (80) trail cam surfaces (779) such that wedge sled (778) will drive staples (77) through a given region of tissue before that particular region of tissue is cut by blade (480) or knife member (80). The stapling and cutting action may still be substantially simultaneous at that region of tissue because wedge sled (778) is configured such that the difference in timing between stapling and cutting is substantially short.

Once instrument (10) has been fired, cartridge (70, 270) may be removed along with blade (780) such that a new cartridge (70, 270, 470, 570) may be inserted into lower jaw (50). It should be understood that cartridge (70, 270) may be replaced with an identical cartridge (70, 270) or a different cartridge (70, 270, 470, 570). For instance, like with wedge sled (378, 478, 578, 678) discussed above, some cartridges (570) may be equipped with blades (780) configured for different procedures such as those described above.

IV. Miscellaneous

It should be understood that in the various examples described above, an articulation joint is configured to permit an end effector to articulate along a first plane and thereby deflect away from the longitudinal axis of a shaft assembly. A locking assembly is operable to selectively lock the articulation joint. The locking assembly includes a locking member that is movable along a second plane to selectively engage the first locking member and thereby lock the articulation joint. The second plane is offset from the first plane. The second plane is also non-parallel with the first plane. In some instances, the second locking member is movable along a second axis that is perpendicular to the longitudinal axis of the shaft assembly. An unlocking member may selectively drive the locking member. The unlocking member may move along a third plane, which may be offset from and/or in a non-parallel relationship with the first and/or second plane(s). The unlocking member may move along a third axis, which may be perpendicular to the longitudinal axis of the shaft assembly and/or the second axis.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims. It should also be understood that the various teachings herein may be readily combined with the teachings of the various references that are cited herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled ARTICULATED SURGICAL INSTRUMENT FOR PERFORMING MINIMALLY INVASIVE SURGERY WITH ENHANCED DEXTERITY AND SENSITIVITY, issued Aug. 11, 1998, the disclosure of which is incorporated by reference herein; U.S. Pat. No. 5,817,084, entitled REMOTE CENTER POSITIONING DEVICE WITH FLEXIBLE DRIVE, issued Oct. 6, 1998, the disclosure of which is incorporated by reference herein; U.S. Pat. No. 5,878,193, entitled AUTOMATED ENDOSCOPE SYSTEM FOR OPTIMAL POSITIONING, issued Mar. 2, 1999, the disclosure of which is incorporated by reference herein; U.S. Pat. No. 6,231,565, entitled ROBOTIC ARM DLUS FOR PERFORMING SURGICAL TASKS, issued May 15, 2001, the disclosure of which is incorporated by reference herein; U.S. Pat. No. 6,783,524, entitled ROBOTIC SURGICAL TOOL WITH ULTRASOUND CAUTERIZING AND CUTTING INSTRUMENT, issued Aug. 31, 2004, the disclosure of which is incorporated by reference herein; U.S. Pat. No. 6,364,888, entitled ALIGNMENT OF MASTER AND SLAVE IN A MINIMALLY INVASIVE SURGICAL APPARATUS, issued Apr. 2, 2002, the disclosure of which is incorporated by reference herein; U.S. Pat. No. 7,524,320, entitled MECHANICAL ACTUATOR INTERFACE SYSTEM FOR ROBOTIC SURGICAL TOOLS, issued Apr. 28, 2009, the disclosure of which is incorporated by reference herein; U.S. Pat. No. 7,691,098, entitled PLATFORM LINK WRIST MECHANISM, issued Apr. 6, 2010, the disclosure of which is incorporated by reference herein; U.S. Pat. No. 7,806,891, entitled REPOSITIONING AND REORIENTATION OF MASTER/SLAVE RELATIONSHIP IN MINIMALLY INVASIVE TELESURGERY, issued Oct. 5, 2010, the disclosure of which is incorporated by reference herein; U.S. Patent Application Publication No. 2013/0012957, entitled AUTOMATED END EFFECTOR COMPONENT RELOADING SYSTEM FOR USE WITH A ROBOTIC SYSTEM, published Jan. 10, 2013, now U.S. Pat. No. 8,844,789, the disclosure of which is incorporated by reference herein; U.S. Patent Application Publication No. 2012/0199630, entitled ROBOTICALLY-CONTROLLED SURGICAL INSTRUMENT WITH FORCE-FEEDBACK CAPABILITIES, published Aug. 9, 2012, now U.S. Pat. No. 8,820,605, the disclosure of which is incorporated by reference herein; U.S. Patent Application Publication No. 2012/0132450, entitled SHIFTABLE DRIVE INTERFACE FOR ROBOTICALLY-CONTROLLED SURGICAL TOOL, published May 31, 2012, now U.S. Pat. No. 8,616,431, the disclosure of which is incorporated by reference herein; U.S. Patent Application Publication No. 2012/0199633, entitled SURGICAL STAPLING INSTRUMENTS WITH CAM-DRIVEN STAPLE DEPLOYMENT ARRANGEMENTS, published Aug. 9, 2012, now U.S. Pat. No. 8,573,461, the disclosure of which is incorporated by reference herein; U.S. Patent Application Publication No. 2012/0199631, entitled ROBOTICALLY-CONTROLLED MOTORIZED SURGICAL END EFFECTOR SYSTEM WITH ROTARY ACTUATED CLOSURE SYSTEMS HAVING VARIABLE ACTUATION SPEEDS, published Aug. 9, 2012, now U.S. Pat. No. 8,602,288, the disclosure of which is incorporated by reference herein; U.S. Patent Application Publication No. 2012/0199632, entitled ROBOTICALLY-CONTROLLED SURGICAL INSTRUMENT WITH SELECTIVELY ARTICULATABLE END EFFECTOR, published Aug. 9, 2012, now U.S. Pat. No. 9,301,759, the disclosure of which is incorporated by reference herein; U.S. Patent Application Publication No. 2012/0203247, entitled ROBOTICALLY-CONTROLLED SURGICAL END EFFECTOR SYSTEM, published Aug. 9, 2012, now U.S. Pat. No. 8,783,541, the disclosure of which is incorporated by reference herein; U.S. Patent Application Publication No. 2012/0211546, entitled DRIVE INTERFACE FOR OPERABLY COUPLING A MANIPULATABLE SURGICAL TOOL TO A ROBOT, published Aug. 23, 2012, now U.S. Pat. No. 8,479,969; U.S. Patent Application Publication No. 2012/0138660, entitled ROBOTICALLY-CONTROLLED CABLE-BASED SURGICAL END EFFECTORS, published Jun. 7, 2012, now U.S. Pat. No. 8,800,838, the disclosure of which is incorporated by reference herein; and/or U.S. Patent Application Publication No. 2012/0205421, entitled ROBOTICALLY-CONTROLLED SURGICAL END EFFECTOR SYSTEM WITH ROTARY ACTUATED CLOSURE SYSTEMS, published Aug. 16, 2012, now U.S. Pat. No. 8,573,465, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A replaceable staple cartridge, comprising:
- a cartridge body, comprising:
  - a deck; and
  - a plurality of staple cavities defined in said deck, wherein said plurality of staple cavities are positioned in longitudinal rows of staple cavities;
- a plurality of staples removably stored in said plurality of staple cavities; and
- a sled movable from a proximal unfired position to a distal fired position through a distal firing stroke to eject said plurality of staples from said plurality of staple cavities, wherein said sled comprises a knife movable within said cartridge body, wherein said knife comprises a knife edge movable along a path between a shielded position and a deployed position, wherein said path comprises a linear path, and wherein said knife edge is configured to translate along the linear path to the shielded position in the distal fired position of said sled subsequent to completion of the distal firing stroke.

2. The replaceable staple cartridge of claim 1, wherein said knife is slidably secured to said sled.

3. The replaceable staple cartridge of claim 1, wherein said knife edge, in the shielded position, is positioned below said deck, and, in the deployed position, extends above said deck.

4. The replaceable staple cartridge of claim 1, wherein said knife edge, in the shielded position, is shielded by said sled.

5. The replaceable staple cartridge of claim 1, wherein said knife further comprises:
- a body comprising said knife edge; and
- a foot pushed toward said deck to move said knife edge away from the shielded position, wherein said foot extends laterally from said body.

6. A stapling instrument, comprising:
- a shaft;
- an end effector extending from said shaft, the end effector comprising a cartridge jaw and an anvil jaw;
- a firing drive comprising a firing beam comprising:
  - a first cam positioned to engage said cartridge jaw; and
  - a second cam positioned to engage said anvil jaw; and
- said replaceable staple cartridge of claim 1, wherein said replaceable staple cartridge is removably seated in said cartridge jaw, and wherein said firing drive further comprises an electric motor configured to drive said firing beam distally through a distal firing stroke.

7. The stapling instrument of claim 6, wherein said sled comprises a proximal push surface, wherein said firing beam is configured to push said proximal push surface to push said sled to the distal fired position, and wherein said firing beam is retractable proximally after said sled is positioned in the distal fired position.

8. A replaceable staple cartridge, comprising:
a cartridge body, comprising:
a deck; and
a plurality of staple cavities defined in said deck, wherein said plurality of staple cavities are positioned in longitudinal rows of staple cavities;
a plurality of staples removably stored in said plurality of staple cavities; and
a sled movable along a longitudinal axis from a proximal unfired position to a distal fired position to eject said plurality of staples from said plurality of staple cavities, wherein said sled comprises a knife movable along said cartridge body, wherein said knife comprises a knife edge moveable along a path between a shielded position and a deployed position, wherein said path comprises a linear path, and wherein said knife edge is movable vertically relative to said longitudinal axis along said path.

9. The replaceable staple cartridge of claim 8, wherein said knife is slidably secured in a slot defined in said sled.

10. The replaceable staple cartridge of claim 8, wherein said knife edge is positioned below said deck when said knife edge is in the shielded position, and wherein said knife edge is translatable into the deployed position, in which said knife edge extends above said deck.

11. The replaceable staple cartridge of claim 8, wherein said knife edge is shielded by said sled when said knife edge is in the shielded position.

12. A stapling instrument, comprising:
a cartridge jaw;
an anvil jaw;
a firing drive comprising a firing beam comprising:
a first cam positioned to engage said cartridge jaw; and
a second cam positioned to engage said anvil jaw; and
said replaceable staple cartridge of claim 8, wherein said replaceable staple cartridge is replaceably seated in said cartridge jaw, wherein said sled comprises a proximal push surface, wherein said firing beam is configured to push said proximal push surface to push said sled to the distal fired position, and wherein said firing beam is retractable proximally after said sled is positioned in the distal fired position.

13. A replaceable staple cartridge, comprising:
a cartridge body, comprising:
a deck; and
a plurality of staple cavities defined in said deck, wherein said plurality of staple cavities are positioned in longitudinal rows of staple cavities;
a plurality of staples removably stored in said plurality of staple cavities; and
a sled movable from a proximal unfired position to a distal fired position to eject said plurality of staples from said plurality of staple cavities, wherein said sled comprises a knife movable along said cartridge body, wherein said knife comprises a knife edge moveable along a path between a shielded position and a deployed position, wherein said path comprises a linear path, and wherein said knife further comprises:
a body comprising said knife edge; and
a foot pushed toward said deck to move said knife edge away from the shielded position, wherein said foot extends laterally from said body.

14. A stapling instrument, comprising:
a cartridge jaw;
an anvil jaw;
a firing drive comprising a firing beam comprising:
a first cam positioned to engage said cartridge jaw; and
a second cam positioned to engage said anvil jaw; and
said replaceable staple cartridge of claim 13, wherein said replaceable staple cartridge is replaceably seated in said cartridge jaw;
wherein said firing beam comprises a motor-driven firing beam.

15. A replaceable staple cartridge, comprising:
a deck;
a plurality of staple cavities defined in said deck, wherein said plurality of staple cavities are positioned in longitudinal rows of staple cavities;
a plurality of staples removably stored in said plurality of staple cavities; and
a sled movable from a proximal unfired position to a distal fired position during a firing stroke to eject said staples from said staple cavities, wherein said sled comprises:
a body defining a slot; and
a knife slidably retained in said slot and carried by said sled during the firing stroke, wherein said knife comprises a knife edge positioned in a shielded configuration outside of the firing stroke, wherein said knife edge is moveable along a path between the shielded configuration and a deployed configuration, and wherein the path comprises a linear path.

16. The replaceable staple cartridge of claim 15, wherein, in the shielded configuration, the knife edge is not exposed for cutting tissue, and wherein, in the deployed configuration, the knife edge is exposed for cutting tissue.

17. The replaceable staple cartridge of claim 16, wherein, in the shielded configuration, the knife edge is shielded by the sled.

18. A stapling instrument, comprising:
said replaceable staple cartridge of claim 15;
a cartridge jaw to receive said replaceable staple cartridge;
an anvil jaw; and
a firing drive comprising a firing beam comprising:
a first cam positioned to engage said cartridge jaw; and
a second cam positioned to engage said anvil jaw.

* * * * *